United States Patent
Zhi et al.

(10) Patent No.: US 8,680,150 B2
(45) Date of Patent: Mar. 25, 2014

(54) SMALL MOLECULE HEMATOPOIETIC GROWTH FACTOR MIMETIC COMPOUNDS THAT ACTIVATE HEMATOPOIETIC GROWTH FACTOR RECEPTORS

(75) Inventors: Lin Zhi, San Diego, CA (US); Andrew R. Hudson, San Diego, CA (US); Cornelis A. Van Oeveren, San Diego, CA (US); Steven L. Roach, San Diego, CA (US); Jason C. Pickens, San Diego, CA (US); Yixing Shen, Encinitas, CA (US); Catalina Cuervo, San Diego, CA (US); Lino J. Valdez, San Diego, CA (US); Jillian Basinger, San Diego, CA (US); Virgina H. Grant, Vista, CA (US)

(73) Assignee: Ligand Pharmaceuticals, Inc., San Diego, CA (US)

( * ) Notice: Subject to any disclaimer, the term of this patent is extended or adjusted under 35 U.S.C. 154(b) by 176 days.

(21) Appl. No.: 12/775,331

(22) Filed: May 6, 2010

(65) Prior Publication Data

US 2011/0003851 A1 Jan. 6, 2011

Related U.S. Application Data

(60) Provisional application No. 61/182,060, filed on May 28, 2009.

(51) Int. Cl.
*A61K 31/16* (2006.01)
*A61K 31/165* (2006.01)

(52) U.S. Cl.
USPC .......................... 514/615; 514/617; 564/161

(58) Field of Classification Search
USPC .................... 514/615, 617; 564/161
See application file for complete search history.

(56) References Cited

U.S. PATENT DOCUMENTS

| | | | |
|---|---|---|---|
| 4,334,015 A * | 6/1982 | Yarian | ........................... 503/218 |
| 5,766,581 A | 6/1998 | Bartley et al. | |
| 6,031,072 A | 2/2000 | Blaschuk et al. | |
| 6,169,071 B1 | 1/2001 | Blaschuk et al. | |
| 6,207,639 B1 | 3/2001 | Blaschuk et al. | |
| 6,326,352 B1 | 12/2001 | Blaschuk et al. | |
| 6,333,307 B1 | 12/2001 | Blaschuk et al. | |
| 6,346,512 B1 | 2/2002 | Blaschuk et al. | |
| 6,417,325 B1 | 7/2002 | Blaschuk et al. | |
| 6,465,427 B1 | 10/2002 | Blaschuk et al. | |
| 6,552,008 B1 | 4/2003 | Duffy et al. | |
| 6,562,786 B1 | 5/2003 | Blaschuk et al. | |
| 6,610,821 B1 | 8/2003 | Blaschuk et al. | |
| 6,642,265 B1 | 11/2003 | Luengo et al. | |
| 6,660,737 B2 | 12/2003 | Almstead et al. | |
| 6,670,387 B1 | 12/2003 | Luengo et al. | |
| 6,720,345 B1 | 4/2004 | Luengo et al. | |
| 6,770,663 B2 | 8/2004 | Wagle et al. | |
| 6,780,845 B2 | 8/2004 | Blaschuk et al. | |
| 6,875,786 B2 | 4/2005 | Duffy et al. | |
| 6,878,729 B2 | 4/2005 | Almstead et al. | |
| 6,914,044 B2 | 7/2005 | Blaschuk et al. | |
| 6,967,238 B2 | 11/2005 | Blaschuk et al. | |
| 7,026,334 B1 | 4/2006 | Takemoto et al. | |
| 7,122,623 B2 | 10/2006 | Blaschuk et al. | |
| 7,138,369 B2 | 11/2006 | Blaschuk et al. | |
| 7,160,870 B2 | 1/2007 | Duffy et al. | |
| 7,268,115 B2 | 9/2007 | Gour et al. | |
| 7,314,887 B2 | 1/2008 | Chen et al. | |
| 7,446,120 B2 | 11/2008 | Gour et al. | |
| 2002/0151475 A1 | 10/2002 | Blaschuk et al. | |
| 2002/0168761 A1 | 11/2002 | Ali et al. | |
| 2003/0065136 A1 | 4/2003 | Ali et al. | |
| 2003/0087811 A1 | 5/2003 | Blaschuk et al. | |
| 2003/0195231 A1 | 10/2003 | Shiota et al. | |
| 2003/0224978 A1 | 12/2003 | Blaschuk et al. | |
| 2004/0006011 A1 | 1/2004 | Gour et al. | |
| 2004/0058864 A1 | 3/2004 | Ali et al. | |
| 2004/0058990 A1 | 3/2004 | Duffy et al. | |
| 2004/0063764 A1 | 4/2004 | Shiota et al. | |
| 2004/0082626 A1 | 4/2004 | Takemoto et al. | |
| 2004/0106545 A1 | 6/2004 | Ali et al. | |
| 2005/0153977 A1 | 7/2005 | Sugasawa et al. | |
| 2006/0069140 A1 | 3/2006 | Miyaji et al. | |
| 2006/0094694 A1 | 5/2006 | Owada et al. | |
| 2006/0183884 A1 | 8/2006 | Blaschuk et al. | |
| 2007/0037785 A1 | 2/2007 | Ansorge et al. | |
| 2008/0081831 A1 | 4/2008 | Gour et al. | |

FOREIGN PATENT DOCUMENTS

| | | |
|---|---|---|
| AU | 33322/97 | 2/1998 |
| AU | 18664/99 | 7/1999 |
| AU | 31154/01 | 7/2001 |
| AU | 53333/01 | 10/2001 |
| AU | 2004281959 | 7/2009 |
| CA | 2259966 | 1/1998 |

(Continued)

OTHER PUBLICATIONS

Ito N, Tamano S, Shirai T. A medium-term rat liver bioassay for rapid in vivo detection of carcinogenic potential of chemicals. Cancer Sci. Jan. 2003;94(1):3-8.*
Bains and Tacke, Curr. Opin, Drug Discov Devel. Jul:6(4):526-43 (2003).
Baser et al., Blood, 89:3118-3128 (1997).
Bojarska-Dahlig, H., "Monoamine Oxidase Inhibitors. III. Hydrazine Derivatives of Certain Arylacetic Acids," Acta Poloniae Pharmaceutica, 1963, vol. 20, No. 4, pp. 293-302 (Polish).

(Continued)

*Primary Examiner* — Paul Zarek
(74) *Attorney, Agent, or Firm* — Knobbe Martens Olson & Bear, LLP

(57) ABSTRACT

The present embodiments relate to compounds with physiological effects, such as the activation of hematopoietic growth factor receptors. The present embodiments also relate to use of the compounds to treat a variety of conditions, diseases and ailments such as hematopoietic conditions and disorders.

13 Claims, No Drawings

(56) References Cited

FOREIGN PATENT DOCUMENTS

| | | |
|---|---|---|
| CA | 2405476 | 10/2001 |
| CA | 2533781 | 2/2005 |
| CA | 2542807 | 4/2005 |
| CN | 1889960 | 1/2007 |
| DE | 10348022 | 5/2005 |
| EP | 1311545 | 5/2003 |
| EP | 1651672 | 5/2006 |
| EP | 1675594 | 7/2006 |
| EP | 0937103 | 11/2007 |
| EP | 1947101 | 7/2008 |
| KR | 20080065285 | 7/2008 |
| WO | WO 98/02452 | 1/1998 |
| WO | WO 99/33875 | 7/1999 |
| WO | WO 01/21180 | 3/2001 |
| WO | WO 01/53331 | 7/2001 |
| WO | WO 01/77146 | 10/2001 |
| WO | WO 03/037905 | 5/2003 |
| WO | WO 03/103686 | 12/2003 |
| WO | WO 2004/033433 | 4/2004 |
| WO | WO 2005/012348 | 2/2005 |
| WO | WO 2005/037779 | 4/2005 |
| WO | WO 2005/118551 | 12/2005 |
| WO | WO 2006/033005 | 3/2006 |
| WO | WO 2007/052808 | 5/2007 |
| WO | WO 2007/054783 | 5/2007 |
| WO | WO 2007/062078 | 5/2007 |

OTHER PUBLICATIONS

Bowman et al., "Small Molecule Inhibitors of the MDM2-p53 Interaction Discovered by Ensemble-Based Receptor Models," Journal of the American Chemical Society, 2007, vol. 129, No. 42, pp. 12809-12814.
CAS RN 102603-93-0 STN Entry Date Jun. 7, 1986.
CAS RN 103213-68-9 STN Entry Date Jul. 12, 1986.
CAS RN 104038-51-9 STN Entry Date Aug. 30, 1986.
CAS RN 107543-97-5 STN Entry Date Apr. 11, 1987.
CAS RN 1087400-18-7 STN Entry Date Dec. 21, 2008.
CAS RN 1106-90-7 STN Entry Date Nov. 16, 1984.
CAS RN 1106-91-8 STN Entry Date Nov. 16, 1984.
CAS RN 1106-92-9 STN Entry Date Nov. 16, 1984.
CAS RN 130260-44-5 STN Entry Date Nov. 2, 1990.
CAS RN 17213-43-3 STN Entry Date Nov. 16, 1984.
CAS RN 17426-43-6 STN Entry Date Nov. 16, 1984.
CAS RN 19365-49-2 STN Entry Date Nov. 16, 1984.
CAS RN 214919-36-5 STN Entry Date Dec. 1, 1998.
CAS RN 22277-80-1 STN Entry Date Nov. 16, 1984.
CAS RN 22277-85-6 STN Entry Date Nov. 16, 1984.
CAS RN 346721-08-2 STN Entry Date Jul. 19, 2001.
CAS RN 416881-13-5 STN Entry Date May 16, 2002.
CAS RN 89399-43-9 STN Entry Date Nov. 16, 1984.
CAS RN 98223-06-4 STN Entry Date Sep. 29, 1985.
Chemical Abstracts Accession No. 1965:16315.
de Sauvage et al., Nature 369:533-538 (1994).
Degen, L. et al," Antimicrobial Activity of a Series of New 5-Nitro-2-furaldehyde Aminoacethydrazones," Chemotherapy, 1972, vol. 17, No. 2, pp. 130-140.
Fanucchi et al., New Engl. J. Med., 336:404-409 (1997).
Fingl et al., "The Pharmacological Basis of Theraputics," Ch. 1 p. 1, 1975.
Greene and Wuts, Protective groups in Organic Synthesis, 3rd ed., John Wiey & Sons, New York, NY, 1999.
Jelkmann, Internal Medicine, vol. 43, No. 8 (Aug. 2004).
Komatsu, Blood, vol. 82(2):456-464, 1993.
Kuter et al., Proc. Natl. Acadm. Sci., 91:11104-11108 (1994).
Kuter et al., The Oncologist, 1:98-106 (1996).
Lok et al., Nature 369:565-568 (1994).
Metcalf, Nature 369:519-520 (1994).
Remington's Pharmaceutical Sciences, Mack Publishing Co., Easton, PA, 18th Ed. 1990.
Sambrook et al., Molecular Cloning: A Laboratory Manual (2d ed., Cold Spring Harbor Laboratory Press, Cold Spring Harbor, N.Y. 1989.
Tacke and Zilch, Endeavour, New Series, 10:191-197 (1986).
Vigon et al., Proc. Natl. Acad. Sci., 89:5640-5644 (1992).
Wending et al., Nature, 369: 571-574 (1994).
Wendling, et al., Biotherapy 10(4):269-77 (1998).

* cited by examiner

SMALL MOLECULE HEMATOPOIETIC GROWTH FACTOR MIMETIC COMPOUNDS THAT ACTIVATE HEMATOPOIETIC GROWTH FACTOR RECEPTORS

CROSS-REFERENCE TO RELATED APPLICATIONS

This application claims benefit of U.S. Provisional Application No. 61/182,060, filed on May 28, 2009, which is incorporated herein by reference in its entirety.

BACKGROUND OF THE INVENTION

1. Field of the Invention

The present embodiments relate to compounds with physiological effects, such as the activation of hematopoietic growth factor receptors. The present embodiments also relate to use of the compounds to treat a variety of conditions, diseases and ailments such as hematopoietic conditions and disorders.

2. Description of the Related Art

Hematopoietic growth factor (HGF) represents a family of biological molecules such as glycoproteins with important regulatory functions in the processes of proliferation, differentiation, and functional activation of hematopoietic progenitors and mature blood cells. HGF compounds can be potent regulators of blood cell proliferation and development in the bone marrow. They are able to augment hematopoiesis when bone marrow dysfunction exists. Recombinant DNA technology has made it possible to clone the genes responsible for many of these factors.

One example of an HGF is Thrombopoietin (TPO), also referred to as c-Mpl ligand, mpl ligand, megapoietin, and megakaryocyte growth and development factor, is a glycoprotein that has been shown to be involved in production of platelets. See e.g., Wendling, F., et. al., Biotherapy 10(4):269-77 (1998); Kuter D. J. et al., The Oncologist, 1:98-106 (1996); Metcalf, Nature 369: 519-520 (1994), all of which are incorporated herein by reference in their entirety. TPO has been cloned and its amino acid sequence and the cDNA sequence encoding it have been described. See e.g., U.S. Pat. No. 5,766,581; Kuter, D. J. et al., Proc. Natl. Acad. Sci., 91:11104-11108 (1994); de Sauvage F. V., et al., Nature, 369: 533-538 (1994); Lok, S. et al., Nature 369:565-568 (1994); Wending, F. et al., Nature, 369: 571-574 (1994), all of which are incorporated herein by reference in their entirety.

In certain instances, TPO activity results from binding of TPO to the TPO receptor (also called MPL). The TPO receptor has been cloned and its amino acid sequence has been described. See e.g., Vigon et al., Proc. Natl. Acad. Sci., 89:5640-5644 (1992), which is incorporated herein by reference in its entirety.

In certain instances, TPO modulators may be useful in treating a variety of hematopoietic conditions, including, but not limited to, thrombocytopenia. See e.g., Baser et al. Blood 89:3118-3128 (1997); Fanucchi et al. New Engl. J. Med. 336:404-409 (1997), both of which are incorporated herein by reference in their entirety. For example, patients undergoing certain chemotherapies, including but not limited to chemotherapy and/or radiation therapy for the treatment of cancer, may have reduced platelet levels. In certain instances, treating such patients with a selective TPO modulator increases platelet levels. In certain instances, selective TPO modulators stimulate production of glial cells, which may result in repair of damaged nerve cells.

Another example of an HGF is the glycoprotein hormone erythropoietin (EPO). EPO is an essential viability and growth factor for the erythrocytic progenitors. EPO is a member of the family of class I cytokines which fold into a compact globular structure consisting of 4 α-helical bundles. Its molecular mass is 30.4 kDa, although it migrates with an apparent size of 34-38 kDa on SDS-polyacrylamide gels. The peptide core of 165 amino acids suffices for receptor-binding and in vitro stimulation of erythropoiesis, while the carbohydrate portion (40% of the total molecule) is required for the in vivo survival of the hormone. The 4 carbohydrate chains of EPO have been analyzed in detail. The 3 complex-type N-linked oligosaccharides at asparagines 24, 38 and 83 appear involved in stabilizing EPO in circulation. EPO is mainly produced by hepatocytes during the fetal stage. After birth, almost all circulating EPO originates from peritubular fibroblast-like cells located in the cortex of the kidneys. Transcription factors of the GATA-family may be important in the control of the time-specific and tissue-specific expression of the EPO gene. In adults, minor amounts of EPO mRNA are expressed in liver parenchyma, spleen, lung, testis and brain. In brain, EPO exerts neurotrophic and neuroprotective effects, which are separate from the action of circulating EPO on erythropoietic tissues. See e.g., Jelkmann, W., *Internal Medicine* Vol. 43, No. 8 (August 2004).

SUMMARY OF THE INVENTION

In certain embodiments, the present embodiments provide a compound of Formula I:

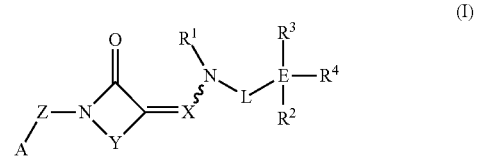

(I)

wherein:

$R^1$ is selected from the group consisting of hydrogen, an optionally substituted $C_1$-$C_6$ alkyl, an optionally substituted $C_1$-$C_6$ haloalkyl, and an optionally substituted $C_1$-$C_6$ heteroalkyl;

$R^2$ is selected from the group consisting of hydrogen, halogen, $OR^C$, $NR^C R^D$, $SR^C$, $NO_2$, CN, $(CH_2)_m R^E$, an optionally substituted $C_1$-$C_6$ alkyl, an optionally substituted $C_1$-$C_6$ haloalkyl, and an optionally substituted $C_1$-$C_6$ heteroalkyl;

$R^3$ is selected from the group consisting of hydrogen, halogen, $OR^A$, $NR^A R^B$, and $SR^A$; or $R^1$ and $R^3$ are linked to form an optionally substituted heterocycle;

$R^4$ is selected from the group consisting of hydrogen, halogen, an optionally substituted $C_1$-$C_8$ alkyl, an optionally substituted $C_1$-$C_8$ haloalkyl, an optionally substituted $C_1$-$C_8$ heteroalkyl, and $(CH_2)_m R^E$;

$R^5$ is selected from the group consisting of hydrogen, an optionally substituted $C_1$-$C_6$ alkyl, an optionally substituted $C_1$-$C_6$ haloalkyl, and an optionally substituted $C_1$-$C_6$ heteroalkyl;

$R^A$ is selected from the group consisting of hydrogen, $C_1$-$C_6$ alkyl, $C_1$-$C_6$ haloalkyl, $C_1$-$C_6$ heteroalkyl, and $C_1$-$C_6$ heterohaloalkyl;

$R^B$ is selected from the group consisting of hydrogen, $SO_2 R^F$, $COR^F$, $CONR^C R^D$, $C_1$-$C_6$ alkyl, $C_1$-$C_6$ haloalkyl, $C_1$-$C_6$ heteroalkyl, and $C_1$-$C_6$ heterohaloalkyl;

$R^C$ and $R^D$ are each independently selected from the group consisting of hydrogen, an optionally substituted $C_1$-$C_6$ alkyl, an optionally substituted $C_1$-$C_6$ haloalkyl, an optionally substituted $C_1$-$C_6$ heteroalkyl, and $(CH_2)_m R^E$; or one of $R^C$ and $R^D$ is an optionally substituted $C_2$-$C_6$ alkyl and the other of $R^C$ and $R^D$ is null; or $R^C$ and $R^D$ are linked to form an optionally substituted $C_3$-$C_8$ ring;

$R^E$ is selected from the group consisting of an optionally substituted aryl and an optionally substituted heteroaryl;

$R^F$ is selected from the group consisting of hydrogen, $C_1$-$C_3$ alkyl, $C_1$-$C_3$ haloalkyl, and an optionally substituted aryl or heteroaryl;

A is selected from the group consisting of an optionally substituted $C_1$-$C_6$ alkyl, an optionally substituted $C_1$-$C_6$ haloalkyl, an optionally substituted $C_1$-$C_6$ heteroalkyl, and $(CH_2)_m R^E$;

E is a monocyclic or bicyclic aromatic ring optionally containing one or more heteroatoms, and optionally fused with a nonaromatic heterocycle or carbocycle;

L is selected from the group consisting of null, $C(R^A)_2$, CO, $CONR^A$, $NR^A CO$, $NR^A CS$, $NR^A C(S)NR^B$ and an optionally substituted $C_1$-$C_6$ heteroalkyl;

X is N or $CR^5$;

Y is selected from the group consisting of a 1-4 atom spacer comprising one or more groups selected from an optionally substituted $C_1$-$C_6$ alkyl, an optionally substituted $C_1$-$C_6$ heteroalkyl, an optionally substituted phenyl, and an optionally substituted heteroaryl;

Z is selected from the group consisting of null, a 2-5 atom spacer selected from an optionally substituted $C_6$-$C_{10}$ aryl and an optionally substituted $C_1$-$C_8$ heteroaryl, and a 1-5 atom spacer of selected from an optionally substituted $C_1$-$C_6$ alkyl, an optionally substituted $C_1$-$C_6$ heteroalkyl, and an optionally substituted $C_1$-$C_6$ haloalkyl; and m is 0, 1, or 2.

Certain embodiments relate to compounds with the following structures:

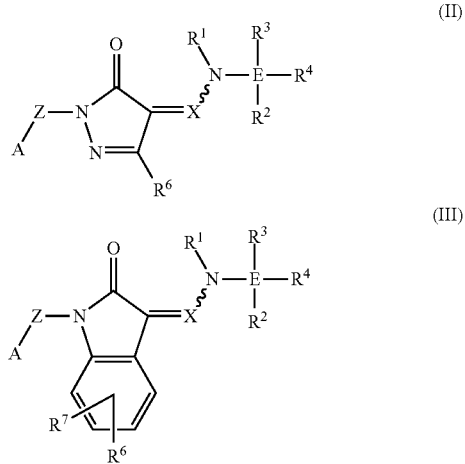

wherein:

$R^1$ selected from the group consisting of hydrogen, an optionally substituted $C_1$-$C_6$ alkyl, an optionally substituted $C_1$-$C_6$ haloalkyl, and an optionally substituted $C_1$-$C_6$ heteroalkyl;

$R^2$ is selected from the group consisting of hydrogen, halogen, $OR^C$, $NR^C R^D$, $SR^C$, $NO_2$, CN, $(CH_2)_m R^E$, an optionally substituted $C_1$-$C_6$ alkyl, an optionally substituted $C_1$-$C_6$ haloalkyl, and an optionally substituted $C_1$-$C_6$ heteroalkyl; or $R^2$ and $R^1$ are linked to form an optionally substituted $C_5$-$C_8$ ring;

$R^3$ is selected from the group consisting of hydrogen, halogen, $OR^A$, $NR^A R^B$, and $SR^A$; or $R^1$ and $R^2$ are linked to form an optionally substituted heterocycle;

$R^4$ is selected from the group consisting of hydrogen, halogen, an optionally substituted $C_1$-$C_8$ alkyl, an optionally substituted $C_1$-$C_8$ haloalkyl, an optionally substituted $C_1$-$C_8$ heteroalkyl, and $(CH_2)_m R^E$;

$R^5$ selected from the group consisting of hydrogen, an optionally substituted $C_1$-$C_6$ alkyl, an optionally substituted $C_1$-$C_6$ haloalkyl, and an optionally substituted $C_1$-$C_6$ heteroalkyl;

$R^6$ is selected from the group consisting of hydrogen, halogen, $OR^C$, $NR^C R^D$, $NO_2$, CN, $CO_2 R^A$, $CONR^C R^D$, $(CH_2)_m R^E$, an optionally substituted $C_1$-$C_6$ alkyl, an optionally substituted $C_1$-$C_6$ haloalkyl, and an optionally substituted $C_1$-$C_6$ heteroalkyl;

$R^7$ is selected from the group consisting of hydrogen, halogen, an optionally substituted $C_1$-$C_6$ alkyl, an optionally substituted $C_1$-$C_6$ haloalkyl, an optionally substituted $C_1$-$C_6$ heteroalkyl, and an optionally substituted aryl or heteroaryl;

$R^A$ is selected from the group consisting of hydrogen, $C_1$-$C_6$ alkyl, $C_1$-$C_6$ haloalkyl, $C_1$-$C_6$ heteroalkyl, and $C_1$-$C_6$ heterohaloalkyl;

$R^B$ is selected from hydrogen, $SO_2 R^F$, $COR^F$, $CONR^C R^D$, $C_1$-$C_6$ alkyl, $C_1$-$C_6$ haloalkyl, $C_1$-$C_6$ heteroalkyl, and $C_1$-$C_6$ heterohaloalkyl;

$R^C$ and $R^D$ are each independently selected from the group consisting of hydrogen, an optionally substituted $C_1$-$C_6$ alkyl, an optionally substituted $C_1$-$C_6$ haloalkyl, an optionally substituted $C_1$-$C_6$ heteroalkyl, and $(CH_2)_m R^E$; or one of $R^C$ and $R^D$ is an optionally substituted $C_2$-$C_6$ alkyl and the other of $R^C$ and $R^D$ is null; or $R^C$ and $R^D$ are linked to form an optionally substituted $C_3$-$C_8$ ring;

$R^E$ is selected from an optionally substituted aryl and an optionally substituted heteroaryl;

$R^F$ is selected from the group consisting of hydrogen, $C_1$-$C_3$ alkyl, $C_1$-$C_3$ haloalkyl, and an optionally substituted aryl or heteroaryl;

A is selected from the group consisting of an optionally substituted $C_1$-$C_6$ alkyl, an optionally substituted $C_1$-$C_6$ haloalkyl, an optionally substituted $C_1$-$C_6$ heteroalkyl, and $(CH_2)_m R^E$;

E is a monocyclic or bicyclic aromatic ring optionally containing one or more heteroatoms, and optionally fused with a nonaromatic heterocycle or carbocycle;

X is N or $CR^5$;

Z is selected from the group consisting of null, a 2-5 atom spacer selected from an optionally substituted $C_6$-$C_{10}$ aryl and an optionally substituted $C_1$-$C_8$ heteroaryl, and a 1-5 atom spacer of selected from an optionally substituted $C_1$-$C_6$ alkyl, an optionally substituted $C_1$-$C_6$ heteroalkyl, and an optionally substituted $C_1$-$C_6$ haloalkyl; and m is 0, 1, or 2;

with the proviso that none of $R^2$, $R^3$, and $R^4$ of the formula II is —$(CH_2)_{0-6}$—OH when it is at the ortho position;

with the proviso that none of $R^2$, $R^3$, $R^4$, and substituents of A or Z contain a carboxylic acid or carboxylic acid derivative or a carboxylic acid bioisostere.

In certain embodiments, the compounds with the following structures are provided:

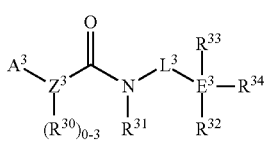

(IV)

wherein:

R³⁰ is selected from the group consisting of hydrogen, halogen, $OR^C$, $NR^CR^D$; $SR^C$, $NO_2$, CN, an optionally substituted $C_1$-$C_6$ alkyl, an optionally substituted $C_1$-$C_6$ haloalkyl, and an optionally substituted $C_1$-$C_6$ heteroalkyl;

R³¹ selected from the group consisting of hydrogen, an optionally substituted $C_1$-$C_6$ alkyl, an optionally substituted $C_1$-$C_6$ haloalkyl, and an optionally substituted $C_1$-$C_6$ heteroalkyl;

R³² is selected from the group consisting of hydrogen, halogen, $OR^C$, $NR^CR^D$; $SR^C$, $NO_2$, CN, an optionally substituted $C_1$-$C_6$ alkyl, an optionally substituted $C_1$-$C_6$ haloalkyl, and an optionally substituted $C_1$-$C_{10}$ heteroalkyl;

R³³ is selected from the group consisting of hydrogen, halogen, $OR^A$, $NR^AR^B$, and $SR^A$; or R³¹ and R³³ are linked to form an optionally substituted heterocycle;

R³⁴ is selected from the group consisting of hydrogen, halogen, an optionally substituted $C_1$-$C_8$ alkyl, an optionally substituted $C_1$-$C_8$ haloalkyl, an optionally substituted $C_1$-$C_8$ heteroalkyl, $(CH_2)_m R^E$, and $CH_2O(CH_2)_m R^E$;

$R^A$ is selected from the group consisting of hydrogen, $C_1$-$C_6$ alkyl, $C_1$-$C_6$ haloalkyl, $C_1$-$C_6$ heteroalkyl, and $C_1$-$C_6$ heterohaloalkyl;

$R^B$ is selected from the group consisting of hydrogen, $SO_2R^F$, $COR^F$, $CONR^CR^D$, $C_1$-$C_6$ alkyl, $C_1$-$C_6$ haloalkyl, $C_1$-$C_6$ heteroalkyl, and $C_1$-$C_6$ heterohaloalkyl;

$R^C$ and $R^D$ are each independently selected from the group consisting of hydrogen, an optionally substituted $C_1$-$C_6$ alkyl, an optionally substituted $C_1$-$C_6$ haloalkyl, an optionally substituted $C_1$-$C_6$ heteroalkyl, and $(CH_2)_m R^E$; or one of $R^C$ and $R^D$ is an optionally substituted $C_2$-$C_6$ alkyl and the other of $R^C$ and $R^D$ is null; or $R^C$ and $R^D$ are linked to form an optionally substituted $C_3$-$C_8$ ring;

$R^E$ is selected from an optionally substituted aryl and an optionally substituted heteroaryl;

$R^F$ is selected from the group consisting of hydrogen, $C_1$-$C_3$ alkyl, $C_1$-$C_3$ haloalkyl, and an optionally substituted aryl or heteroaryl;

A³ is selected from the group consisting of an optionally substituted $C_1$-$C_6$ alkyl, an optionally substituted $C_1$-$C_6$ haloalkyl, an optionally substituted $C_1$-$C_6$ heteroalkyl, a nonaromatic heterocycle, $OR^C$, $NR^AR^B$, and $(CH_2)_m R^E$;

E³ is a monocyclic or bicyclic aromatic ring optionally containing one or more heteroatoms, and optionally fused with a nonaromatic heterocycle or carbocycle;

L³ is selected from the group consisting of $CR^CR^D$, O, S, $NR^A$, $N=CR^C$, an optionally substituted $C_1$-$C_4$ alkyl, an optionally substituted $C_1$-$C_4$ haloalkyl, and an optionally substituted $C_1$-$C_4$ heteroalkyl; or L³ and R³¹ are linked to form an optionally substituted $C_3$-$C_8$ ring;

Z³ is selected from the group consisting of a $C_6$-$C_{10}$ arylalkyl, a $C_6$-$C_{10}$ arylheteroalkyl, a $C_3$-$C_{10}$ arylalkylhetero, a $C_3$-$C_{10}$ heteroarylheteroalkyl, and a monocyclic or bicyclic aromatic ring optionally containing one or more heteroatoms and optionally fused with a nonaromatic heterocycle or carbocycle; and m is 0, 1, or 2.

In certain embodiments, a compound of Formula I, II, III, or IV, is a hematopoietic growth factor mimetic.

In certain embodiments, provided are methods for modulating activity of HGF receptors. Such methods comprise contacting a cell with one or more compounds of the present embodiments. Such methods include, but are not limited to, contacting HGF and/or HGF receptors with one or more compounds of the present embodiments.

In certain embodiments, the embodiments provide a method for identifying a compound that is capable of modulating HGF activity comprising: a) contacting a cell capable of a HGF activity with a compound of the present embodiments; and b) monitoring an effect on the cell. In certain such embodiments, the cell expresses a HGF receptor.

In certain embodiments, provided are methods of treating a patient comprising administering to the patient a compound of the present embodiments. In certain embodiments, such a patient suffers from thrombocytopenia. In certain embodiments, one or more compounds of the present embodiments are administered to a patient before, during or after chemotherapy, bone marrow transplantation, and/or radiation therapy. In certain embodiments, one or more compounds of the embodiments are administered to a patient suffering from a plastic anemia, bone marrow failure, and/or idiopathic thrombocytopenia. In certain embodiments, one or more compounds of the present embodiments are administered to a patient suffering from a disease of the nervous system. In certain embodiments, one or more compounds of the present embodiments are administered to a patient suffering from amyotrophic lateral sclerosis, multiple sclerosis, or multiple dystrophy. In certain embodiments, one or more compounds of the present embodiments are administered to a patient with a nerve injury, including, but not limited to, a spinal cord injury.

In certain embodiments, provided are pharmaceutical compositions comprising: i) a physiologically acceptable carrier, diluent, or excipient, or a combination thereof; and ii) one or more compounds of the present embodiments.

Certain embodiments provide a selective HGF modulator. Certain embodiments provide a selective HGF receptor agonist. Certain embodiments provide a selective HGF receptor antagonist. Certain embodiments provide a selective HGF partial agonist. Certain embodiments provide a selective HGF receptor binding compound. Certain embodiments provide a HGF mimic.

DETAILED DESCRIPTION OF THE INVENTION

It is to be understood that both the foregoing general description and the following detailed description are exemplary and explanatory only and are not restrictive of the embodiments claimed. In this application, the use of the singular includes the plural unless specifically stated otherwise. In this application, the use of "or" means "and/or" unless stated otherwise. Furthermore, use of the term "including" as well as other forms, such as "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

DEFINITIONS

Unless specific definitions are provided, the nomenclatures utilized in connection with, and the laboratory procedures and techniques of, analytical chemistry, synthetic organic chemistry, and medicinal and pharmaceutical chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, pharmaceutical preparation, formulation, and delivery, and treatment of patients. Standard techniques may be used for recombinant DNA, oligonucleotide synthesis, and tissue culture and transformation (e.g., electroporation, lipofection). Reactions and purification techniques may be performed e.g., using kits according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference in its entirety for any purpose.

As used herein, the following terms are defined with the following meanings, unless expressly stated otherwise.

The term "selective binding compound" refers to a compound that selectively binds to any portion of one or more target.

The term "selective HGF receptor binding compound" refers to a compound that selectively binds to any portion of a HGF receptor.

The term "selectively binds" refers to the ability of a selective binding compound to bind to a target receptor with greater affinity than it binds to a non-target receptor. In certain embodiments, selective binding refers to binding to a target with an affinity that is at least 10, 50, 100, 250, 500, or 1000 times greater than the affinity for a non-target.

The term "target receptor" refers to a receptor or a portion of a receptor capable of being bound by a selective binding compound. In certain embodiments, a target receptor is a HGF receptor.

The term "modulator" refers to a compound that alters an activity. For example, a modulator may cause an increase or decrease in the magnitude of a certain activity compared to the magnitude of the activity in the absence of the modulator. In certain embodiments, a modulator is an inhibitor, which decreases the magnitude of one or more activities. In certain embodiments, an inhibitor completely prevents one or more biological activities. In certain embodiments, a modulator is an activator, which increases the magnitude of at least one activity. In certain embodiments the presence of a modulator results in a activity that does not occur in the absence of the modulator.

The term "selective modulator" refers to a compound that selectively modulates a target activity.

The term "selective HGF modulator" refers to a compound that selectively modulates at least one HGF activity. The term selective HGF modulator includes, but is not limited to "HGF mimic" which refers to a compound, the presence of which results in at least one HGF activity. HGF mimics are described in WO 03/103686A1 and WO 01/21180, both of which are incorporated herein by reference in their entirety.

The term "selectively modulates" refers to the ability of a selective modulator to modulate a target activity to a greater extent than it modulates a non-target activity.

The term "target activity" refers to a biological activity capable of being modulated by a selective modulator. Certain exemplary target activities include, but are not limited to, binding affinity, signal transduction, enzymatic activity, the proliferation and/or differentiation of progenitor cells, generation of platelets, and alleviation of symptoms of a disease or condition.

The term "HGF activity" refers to a biological activity that results, either directly or indirectly from the presence of HGF. Exemplary HGF activities include, but are not limited to, proliferation and or differentiation of progenitor cells to produce platelets; hematopoiesis; growth and/or development of glial cells; repair of nerve cells; and alleviation of thrombocytopenia.

The term "thrombocytopenia" refers to a condition wherein the concentration of platelets in the blood of a patient is below what is considered normal for a healthy patient. In certain embodiments, thrombocytopenia is a platelet count less than 450,000, 400,000, 350,000, 300,000, 250,000, 200,000, 150,000, 140,000, 130,000, 120,000, 110,000, 100,000, 75,000, or 50,000 platelets per microliter of blood.

The term "receptor mediated activity" refers to any biological activity that results, either directly or indirectly, from binding of a ligand to a receptor.

The term "agonist" refers to a compound, the presence of which results in a biological activity of a receptor that is the same as the biological activity resulting from the presence of a naturally occurring ligand for the receptor.

The term "partial agonist" refers to a compound, the presence of which results in a biological activity of a receptor that is of the same type as that resulting from the presence of a naturally occurring ligand for the receptor, but of a lower magnitude.

The term "antagonist" refers to a compound, the presence of which results in a decrease in the magnitude of a biological activity of a receptor. In certain embodiments, the presence of an antagonist results in complete inhibition of a biological activity of a receptor.

The term "alkyl" refers to a branched or unbranched aliphatic hydrocarbon group. An alkyl may be a "saturated alkyl," which means that it does not contain any alkene or alkyne groups. An alkyl group may be an "unsaturated alkyl," which means that it comprises at least one alkene or alkyne group. An alkyl, whether saturated or unsaturated, may be branched or straight chain. Alkyls may be cyclic or non-cyclic. Cyclic alkyls may include multicyclic systems including fused alkyl rings. Alkyls may be substituted or unsubstituted. Alkyls include, but are not limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like, each of which may be optionally substituted.

In certain embodiments, an alkyl comprises 1 to 20 carbon atoms (whenever it appears herein, a numerical range such as "1 to 20" refers to each integer in the given range; e.g., "1 to 20 carbon atoms" means that an alkyl group may comprise only 1 carbon atom, 2 carbon atoms, 3 carbon atoms, etc., up to and including 20 carbon atoms, although the term "alkyl" also includes instances where no numerical range of carbon atoms is designated).

The term "lower alkyl" refers to an alkyl comprising 1 to 5 carbon atoms. The term "medium alkyl" refers to an alkyl comprising 5 to 10 carbon atoms. An alkyl may be designated as "$C_1$-$C_4$ alkyl" or similar designations. By way of example only, "$C_1$-$C_4$ alkyl" indicates an alkyl having one, two, three, or four carbon atoms, e.g., the alkyl is selected from methyl, ethyl, propyl, iso-propyl, n-butyl, iso-butyl, sec-butyl, t-butyl, ethenyl, propenyl, butenyl, ethynyl, propynyl, and butynyl.

The term "alkenyl" refers to an alkyl group comprising at least one carbon-carbon double bond.

The term "alkynyl" refers to an alkyl group comprising at least one carbon-carbon triple bond.

The term "haloalkyl" refers to an alkyl in which at least one hydrogen atom is replaced with a halogen atom. In certain of the embodiments in which two or more hydrogen atom are replaced with halogen atoms, the halogen atoms are all the same as one another. In certain of such embodiments, the halogen atoms are not all the same as one another.

The term "heteroalkyl" refers to a branched or unbranched aliphatic hydrocarbon group comprising one or more oxygen, sulfur, nitrogen, or NH. Examples of heteroalkyls include, but are not limited to, $CH_3C(=O)CH_2—$, $CH_3C(=O)CH_2CH_2—$, $CH_3CH_2C(=O)CH_2CH_2—$, $CH_3C(=O)CH_2CH_2CH_2—$, $CH_3NHC(=O)CH_2—$, $CH_3C(=O)NHCH_2—$, $CH_3OCH_2CH_2—$, $CH_3NHCH_2—$, and the like.

The term "straight-chain alkoxy" refers to a group comprising the formula: $—(CH_2)_pO—$ wherein p is any integer. Straight-chain alkoxy does not include substituted or branched alkoxy groups.

The term "non-straight-chain-alkoxy-heteroalkyl" refers to any heteroalkyl that is not a straight-chain alkoxy heteroalkyl. Thus, for example, non-straight-chain-alkoxy heteroalkyls include, but are not limited to: 2,2-isopropyloxy; 1,2-propyloxy; 1,1-ethyloxy; methylamino; ethylamino; propylamino; methylpyrrolidino; and methylpiperidino.

The term "olefin" refers to a C=C bond.

The term "heterohaloalkyl" refers to a heteroalkyl in which at least one hydrogen atom is replaced with a halogen atom.

The term "carbocycle" refers to a group comprising a covalently closed ring, wherein each of the atoms forming the ring is a carbon atom. Carbocyclic rings may be formed by three, four, five, six, seven, eight, nine, or more than nine carbon atoms. Carbocycles may be optionally substituted.

The term "heterocycle" refers to a group comprising a covalently closed ring wherein at least one atom forming the ring is a heteroatom. Heterocyclic rings may be formed by three, four, five, six, seven, eight, nine, or more than nine atoms. Any number of those atoms may be heteroatoms (i.e., a heterocyclic ring may comprise one, two, three, four, five, six, seven, eight, nine, or more than nine heteroatoms). In heterocyclic rings comprising two or more heteroatoms, those two or more heteroatoms may be the same or different from one another. Heterocycles may be optionally substituted. Binding to a heterocycle can be at a heteroatom or via a carbon atom. For example, binding for benzo-fused derivatives, may be via a carbon of the benzenoid ring. Examples of heterocycles include, but are not limited to the following:

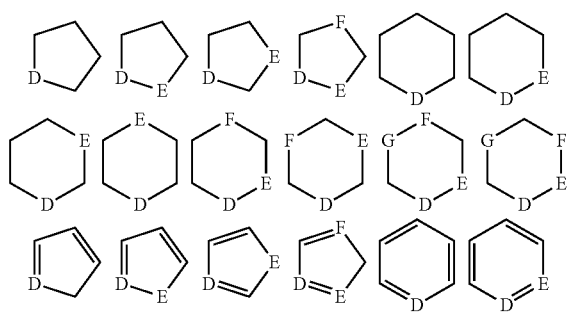

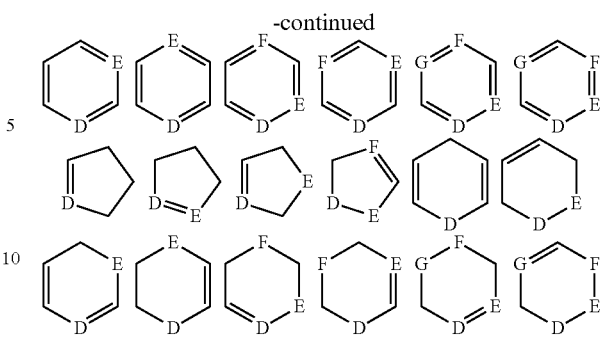

wherein D, E, F, and G independently represent a heteroatom. Each of D, E, F, and G may be the same or different from one another.

The term "heteroatom" refers to an atom other than carbon or hydrogen. Heteroatoms are typically independently selected from oxygen, sulfur, nitrogen, and phosphorus, but are not limited to those atoms. In embodiments in which two or more heteroatoms are present, the two or more heteroatoms may all be the same as one another, or some or all of the two or more heteroatoms may each be different from the others.

The term "aromatic" refers to a group comprising a covalently closed ring having a delocalized π-electron system. Aromatic rings may be formed by five, six, seven, eight, nine, or more than nine atoms. Aromatics may be optionally substituted. Examples of aromatic groups include, but are not limited to phenyl, naphthalenyl, phenanthrenyl, anthracenyl, tetralinyl, fluorenyl, indenyl, and indanyl. The term aromatic includes, for example, benzenoid groups, connected via one of the ring-forming carbon atoms, and optionally carrying one or more substituents selected from an aryl, a heteroaryl, a cycloalkyl, a non-aromatic heterocycle, a halo, a hydroxy, an amino, a cyano, a nitro, an alkylamido, an acyl, a $C_{1-6}$ alkoxy, a $C_{1-6}$ alkyl, a $C_{1-6}$ hydroxyalkyl, a $C_{1-6}$ aminoalkyl, a $C_{1-6}$ alkylamino, an alkylsulfenyl, an alkylsulfinyl, an alkylsulfonyl, an sulfamoyl, or a trifluoromethyl. In certain embodiments, an aromatic group is substituted at one or more of the para, meta, and/or ortho positions. Examples of aromatic groups comprising substitutions include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl, 3-cyanophenyl, 4-cyanophenyl, dimethylphenyl, naphthyl, hydroxynaphthyl, hydroxymethylphenyl, (trifluoromethyl)phenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl.

The term "aryl" refers to an aromatic group wherein each of the atoms forming the ring is a carbon atom. Aryl rings may be formed by five, six, seven, eight, nine, or more than nine carbon atoms. Aryl groups may be optionally substituted.

The term "heteroaryl" refers to an aromatic group wherein at least one atom forming the aromatic ring is a heteroatom. Heteroaryl rings may be formed by three, four, five, six, seven, eight, nine, or more than nine atoms. Heteroaryl groups may be optionally substituted. Examples of heteroaryl groups include, but are not limited to, aromatic $C_{3-8}$ heterocyclic groups comprising one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms. In certain embodiments, heteroaryl groups are optionally substituted with one or more substituents, independently selected from halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl. Examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, O—$C_{1-6}$-alkyl, $C_{1-6}$-alkyl, hydroxy-$C_{1-6}$-alkyl, and amino-$C_{1-6}$-alkyl.

The term "non-aromatic ring" refers to a group comprising a covalently closed ring that does not have a delocalized π-electron system.

The term "cycloalkyl" refers to a group comprising a non-aromatic ring wherein each of the atoms forming the ring is a carbon atom. Cycloalkyl rings may be formed by three, four, five, six, seven, eight, nine, or more than nine carbon atoms. Cycloalkyls may include multicyclic systems (e.g., fused ring systems). Cycloalkyls may be optionally substituted. In certain embodiments, a cycloalkyl comprises one or more unsaturated bonds. Examples of cycloalkyls include, but are not limited to, cyclopropane, cyclobutane, cyclopentane, cyclopentene, cyclopentadiene, cyclohexane, cyclohexene, 1,3-cyclohexadiene, 1,4-cyclohexadiene, cycloheptane, and cycloheptene.

The term "non-aromatic heterocycle" refers to a group comprising a non-aromatic ring wherein one or more atoms forming the ring is a heteroatom and optionally includes one or more carbonyl or thiocarbonyl groups as part of the ring. Non-aromatic heterocyclic rings may be formed by three, four, five, six, seven, eight, nine, or more than nine atoms. Non-aromatic heterocycles may be optionally substituted. Examples of non-aromatic heterocycles include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane.

The term "arylalkyl" refers to a group comprising an aryl group bound to an alkyl group.

The term "carbocycloalkyl" refers to a group comprising a carbocyclic cycloalkyl ring. Carbocycloalkyl rings may be formed by three, four, five, six, seven, eight, nine, or more than nine carbon atoms. Carbocycloalkyl groups may be optionally substituted.

The term "ring" refers to any covalently closed structure. Rings include, for example, carbocycles (e.g., aryls and cycloalkyls), heterocycles (e.g., heteroaryls and non-aromatic heterocycles), aromatics (e.g., aryls and heteroaryls), and non-aromatics (e.g., cycloalkyls and non-aromatic heterocycles). Rings may be optionally substituted. Rings may form part of a ring system.

The term "ring system" refers to a either a single ring or two or more rings, wherein, if two or more rings are present, the two or more of the rings are fused. The term "fused" refers to structures in which two or more rings share one or more bonds.

The term "carboxylic acid bioisostere" refers to a group that is biologically equivalent to a carboxylic acid. For example, carboxylic acid bioisosteres include, but are not limited to, tetrazole, $NHSO_2R^{15}$, $OC(S)NR^{10}R^{11}$, $SC(O)NR^{10}R^{11}$, thiazolidinedione, oxazolidinedione, and 1-oxa-2,4-diazolidine-3,5-dione. In certain embodiments, a carboxylic acid bioisostere comprises the following structure:

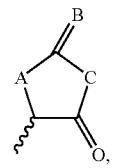

wherein A, 13, and C are each independently selected from O, S, and N.

The term "spacer" refers to an atom or group of atoms that separate two or more groups from one another by a desired number of atoms. For example, in certain embodiments, it may be desirable to separate two or more groups by one, two, three, four, five, six, or more than six atoms. In such embodiments, any atom or group of atoms may be used to separate those groups by the desired number of atoms. Spacers are optionally substituted. In certain embodiments, a spacer comprises saturated or unsaturated alkyls, heteroalkyls and/or haloalkyls. In certain embodiments, a spacer comprises atoms that are part of a ring.

Solely for the purposes of illustration, and without limiting the above definition, some examples of spacers are provided. Examples of 1 atom spacers include, but are not limited to, the following:

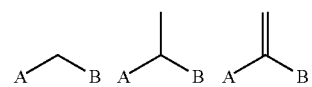

where A and B represent groups which are separated by the desired number of atoms. Examples of 2 atom spacers include, but are not limited to, the following:

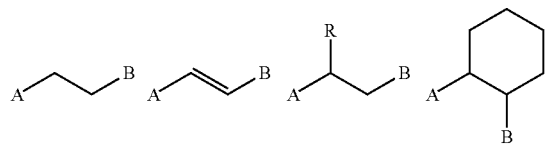

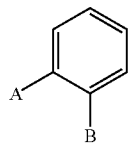

where A and B represent groups which are separated by the desired number of atoms.

Examples of 3 atom spacers include, but are not limited to, the following:

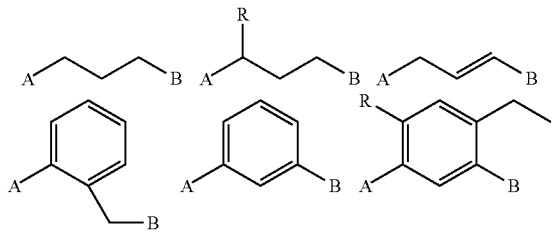

where A and B represent groups which are separated by the desired number of atoms. As is evident from the above examples, the atoms that create the desired separation may themselves be part of a group. That group may be, for example, an alkyl, heteroalkyl, haloalkyl, heterohaloalkyl, cycloalkyl, aryl, arylalkyl, heteroaryl, non-aromatic heterocycle, or substituted alkyl all of which are optionally substituted. Thus the term "1-5 atom spacer" refers to a spacer that separates two groups by 1, 2, 3, 4, or 5 atoms and does not indicate the total size of the group that constitutes the spacer.

As used herein, the term "linked to form a ring" refers to instances where two atoms that are bound either to a single atom or to atoms that are themselves ultimately bound, are each bound to a linking group, such that the resulting structure forms a ring. That resulting ring comprises the two atoms that are linked to form a ring, the atom (or atoms) that previously linked those atoms, and the linker. For example, if A and B below are "linked to form a ring"

the resulting ring includes A, B, C, and a linking group. Unless otherwise indicated, that linking group may be of any length and may be optionally substituted. Referring to the above example, resulting structures include, but are not limited to:

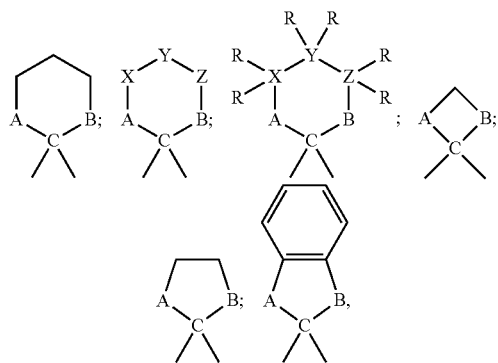

and the like.

In certain embodiments, the two substituents that together form a ring are not immediately bound to the same atom. For example, if A and B, below, are linked to form a ring:

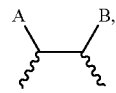

the resulting ring comprises A, B, the two atoms that already link A and B and a linking group. Examples of resulting structures include, but are not limited to:

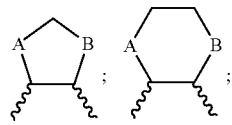

and the like.

In certain embodiments, the atoms that together form a ring are separated by three or more atoms. For example, if A and B, below, are linked to form a ring:

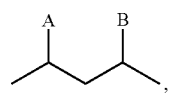

the resulting ring comprises A, B, the 3 atoms that already link A and B, and a linking group. Examples of resulting structures include, but are not limited to:

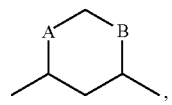

and the like.

As used herein, the term "together form a bond" refers to the instance in which two substituents to neighboring atoms are null the bond between the neighboring atoms becomes a double bond. For example, if A and B below "together form a bond"

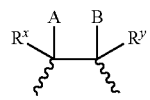

the resulting structure is:

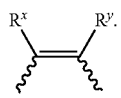

The term "null" refers to a group being absent from a structure. For example, in the structure

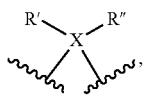

where in certain instances X is N, if X is N, one of R' or R" is null, meaning that only three groups are bound to the N.

The substituent "R" appearing by itself and without a number designation refers to a substituent selected from alkyl, cycloalkyl, aryl, heteroaryl (bonded through a ring carbon) and non-aromatic heterocycle (bonded through a ring carbon).

The term "O-carboxy" refers to the group consisting of formula RC(=O)O—.

The term "C-carboxy" refers to the group consisting of formula —C(=O)OR.

The term "acetyl" refers to the group consisting of formula —C(=O)CH$_3$.

The term "trihalomethanesulfonyl" refers to the group consisting of formula X$_3$CS(=O)$_2$— where X is a halogen.

The term "cyano" refers to the group consisting of formula —CN.

The term "isocyanato" refers to the group consisting of formula —NCO.

The term "thiocyanato" refers to the group consisting of formula —CNS.

The term "isothiocyanato" refers to the group consisting of formula —NCS.

The term "sulfonyl" refers to the group consisting of formula —S(=O)—R.

The term "S-sulfonamido" refers to the group consisting of formula —S(=O)$_2$NR.

The term "N-sulfonamido" refers to the group consisting of formula RS(=O)$_2$NH—.

The term "trihalomethanesulfonamido" refers to the group consisting of formula X$_3$CS(=O)$_2$NR—.

The term "O-carbamyl" refers to the group consisting of formula —OC(=O)—NR.

The term "N-carbamyl" refers to the group consisting of formula ROC(=O)NH—.

The term "O-thiocarbamyl" refers to the group consisting of formula —OC(=S)—NR.

The term "N-thiocarbamyl" refers to the group consisting of formula ROC(=S)NH—.

The term "C-amido" refers to the group consisting of formula —C(=O)—NR$_2$.

The term "N-amido" refers to the group consisting of formula RC(=O)NH—.

The term "oxo" refers to the group consisting of formula =O.

The term "carbonyl" refers to the group consisting of formula —C(=O)R.

The term "thiocarbonyl" refers to the group consisting of formula —C(=S)R.

The term "dihydropyrazolylene" refers to a di-radical of an optionally substituted dihydropyrazole ring, wherein the dihydropyrazole ring has the structure:

and wherein the two radicals may be at any positions on the ring.

The term "pyrazolyl" refers to a radical of a pyrzole ring, wherein the pyrzole ring has the structure:

and wherein the radical may be at any position on the ring.

The term "ester" refers to a chemical moiety with formula —(R)$_n$—COOR', where R and R' are independently selected from alkyl, cycloalkyl, aryl, heteroaryl (bonded through a ring carbon) and non-aromatic heterocycle (bonded through a ring carbon), where n is 0 or 1.

The term "amide" refers to a chemical moiety with formula —(R)$_n$—C(O)NHR' or —(R)$_n$—NHC(O)R', where R and R' are independently selected from alkyl, cycloalkyl, aryl, heteroaryl (bonded through a ring carbon) and heteroalicyclic (bonded through a ring carbon), where n is 0 or 1. In certain embodiments, an amide may be an amino acid or a peptide.

The terms "amine," "hydroxy," and "carboxyl" include such groups that have been esterified or amidified. Procedures and specific groups used to achieve esterification and amidification are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein in its entirety.

Unless otherwise indicated, the term "optionally substituted," refers to a group in which none, one, or more than one of the hydrogen atoms has been replaced with one or more group(s) individually and independently selected from: alkyl, heteroalkyl, haloalkyl, heterohaloalkyl, cycloalkyl, aryl, arylalkyl, heteroaryl, non-aromatic heterocycle, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, oxo, and amino, including mono- and di-substituted amino groups, and the protected derivatives of amino groups. Such protective derivatives (and protecting groups that may form such protective derivatives) are known to those of skill in the art and may be found in references such as Greene and Wuts, above. In embodiments in which two or more hydrogen atoms have been substituted, the substituent groups may together form a ring.

Throughout the specification, groups and substituents thereof can be chosen by one skilled in the field to provide stable moieties and compounds.

The term "carrier" refers to a compound that facilitates the incorporation of another compound into cells or tissues. For example, dimethyl sulfoxide (DMSO) is a commonly used carrier for improving incorporation of certain organic compounds into cells or tissues.

The term "pharmaceutical agent" refers to a chemical compound or composition capable of inducing a desired therapeutic effect in a patient. In certain embodiments, a pharmaceutical agent comprises an active agent, which is the agent that induces the desired therapeutic effect. In certain embodiments, a pharmaceutical agent comprises a prodrug. In certain embodiments, a pharmaceutical agent comprises inactive ingredients such as carriers, excipients, and the like.

The term "therapeutically effective amount" refers to an amount of a pharmaceutical agent sufficient to achieve a desired therapeutic effect.

The term "prodrug" refers to an pharmaceutical agent that is converted from a less active form into a corresponding more active form in vivo.

The term "pharmaceutically acceptable" refers to a formulation of a compound that does not significantly abrogate the biological activity, a pharmacological activity and/or other properties of the compound when the formulated compound is administered to a patient. In certain embodiments, a pharmaceutically acceptable formulation does not cause significant irritation to a patient.

The term "co-administer" refers to administering more than one pharmaceutical agent to a patient. In certain embodiments, co-administered pharmaceutical agents are administered together in a single dosage unit. In certain embodiments, co-administered pharmaceutical agents are administered separately. In certain embodiments, co-administered pharmaceutical agents are administered at the same time. In certain embodiments, co-administered pharmaceutical agents are administered at different times.

The term "patient" includes human and animal subjects.

The term "substantially pure" means an object species (e.g., compound) is the predominant species present (i.e., on a molar basis it is more abundant than any other individual species in the composition). In certain embodiments, a substantially purified fraction is a composition wherein the object species comprises at least about 50 percent (on a molar basis) of all species present. In certain embodiments, a substantially pure composition will comprise more than about 80%, 85%, 90%, 95%, or 99% of all species present in the composition. In certain embodiments, the object species is purified to essential homogeneity (contaminant species cannot be detected in the composition by conventional detection methods) wherein the composition consists essentially of a single species.

The term "tissue-selective" refers to the ability of a compound to modulate a biological activity in one tissue to a greater or lesser degree than it modulates a biological activity in another tissue. The biological activities in the different tissues may be the same or they may be different. The biological activities in the different tissues may be mediated by the same type of target receptor. For example, in certain embodiments, a tissue-selective compound may modulate receptor mediated biological activity in one tissue and fail to modulate, or modulate to a lesser degree, receptor mediated biological activity in another tissue type.

The term "monitoring" refers to observing an effect or absence of any effect. In certain embodiments, one monitors cells after contacting those cells with a compound of the present embodiments. Examples of effects that may be monitored include, but are not limited to, changes in cell phenotype, cell proliferation, receptor activity, or the interaction between a receptor and a compound known to bind to the receptor.

The term "cell phenotype" refers to physical or biological characteristics. Examples of characteristics that constitute phenotype included, but are not limited to, cell size, cell proliferation, cell differentiation, cell survival, apoptosis (cell death), or the utilization of a metabolic nutrient (e.g., glucose uptake). Certain changes or the absence of changes in cell phenotype are readily monitored using techniques known in the art.

The term "cell proliferation" refers to the rate at which cells divide. In certain embodiments, cells are in situ in an organism. In certain embodiments, cells are grown in vitro in a vessel. The number of cells growing in a vessel can be quantified by a person skilled in the art (e.g., by counting cells in a defined area using a microscope or by using laboratory apparatus that measure the density of cells in an appropriate medium). One skilled in that art can calculate cell proliferation by determining the number of cells at two or more times.

The term "contacting" refers to bringing two or more materials into close enough proximity that they may interact. In certain embodiments, contacting can be accomplished in a vessel such as a test tube, a Petri dish, or the like. In certain embodiments, contacting may be performed in the presence of additional materials. In certain embodiments, contacting may be performed in the presence of cells. In certain of such embodiments, one or more of the materials that are being contacted may be inside a cell. Cells may be alive or may dead. Cells may or may not be intact.

Certain Compounds

Certain compounds that modulate one or more HGF activity and/or bind to HGF receptors play a role in health. In certain embodiments, compounds are useful for treating any of a variety of diseases or conditions. A surprising discovery has been made that compounds with activity at the TPO receptor or other specific receptors also have broader HGF activity which can modulate HGF receptors affecting a wide range of diseases and disorders.

Certain embodiments provide selective HGF modulators. Certain embodiments provide selective HGF receptor binding agents. Certain embodiments provide methods of making and methods of using selective HGF modulators and/or selective HGF receptor binding agents. In certain embodiments, selective HGF modulators are agonists, partial agonists, and/or antagonists for the HGF receptor.

The compounds disclosed herein can be used alone or in combination with other agents, for example, to modulate hematopoiesis, erythropoiesis, granulopoiesis, thrombopoiesis, and myelopoiesis. The instant compounds can also be used alone or in combination with other agents in treatment or prevention of a disease or condition caused by abnormal function of hematopoiesis, erythropoiesis, granulopoiesis, thrombopoiesis, and myelopoiesis. Some non-limiting examples of diseases include anemia, neutropenia, thrombocytopenia, cardiovascular disorders, immune/autoimmune disorders, cancers, infectious disorders or diseases, and neurologic disorders.

In certain embodiments, the present embodiments provide a compound of Formula I:

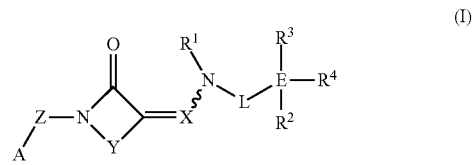

wherein:

$R^1$ is selected from the group consisting of hydrogen, an optionally substituted $C_1$-$C_6$ alkyl, an optionally substituted $C_1$-$C_6$ haloalkyl, and an optionally substituted $C_1$-$C_6$ heteroalkyl;

$R^2$ is selected from the group consisting of hydrogen, halogen, $OR^C$, $NR^CR^D$, $SR^C$, $NO_2$, $CN$, $(CH_2)_mR^E$, an optionally substituted $C_1$-$C_6$ alkyl, an optionally substituted $C_1$-$C_6$ haloalkyl, and an optionally substituted $C_1$-$C_6$ heteroalkyl;

$R^3$ is selected from the group consisting of hydrogen, halogen, $OR^A$, $NR^AR^B$, and $SR^A$; or $R^1$ and $R^3$ are linked to form an optionally substituted heterocycle;

$R^4$ is selected from the group consisting of hydrogen, halogen, an optionally substituted $C_1$-$C_8$ alkyl, an optionally substituted $C_1$-$C_8$ haloalkyl, an optionally substituted $C_1$-$C_8$ heteroalkyl, and $(CH_2)_m R^E$;

$R^5$ is selected from the group consisting of hydrogen, an optionally substituted $C_1$-$C_6$ alkyl, an optionally substituted $C_1$-$C_6$ haloalkyl, and an optionally substituted $C_1$-$C_6$ heteroalkyl;

$R^A$ is selected from the group consisting of hydrogen, $C_1$-$C_6$ alkyl, $C_1$-$C_6$ haloalkyl, $C_1$-$C_6$ heteroalkyl, and $C_1$-$C_6$ heterohaloalkyl;

$R^B$ is selected from the group consisting of hydrogen, $SO_2R^F$, $COR^F$, $CONR^CR^D$, $C_0$ alkyl, $C_1$-$C_6$ haloalkyl, $C_1$-$C_6$ heteroalkyl, and $C_1$-$C_6$ heterohaloalkyl;

$R^C$ and $R^D$ are each independently selected from the group consisting of hydrogen, an optionally substituted $C_1$-$C_6$ alkyl, an optionally substituted $C_1$-$C_6$ haloalkyl, an optionally substituted $C_1$-$C_6$ heteroalkyl, and $(CH_2)_m R^E$; or one of $R^C$ and $R^D$ is an optionally substituted $C_2$-$C_6$ alkyl and the other of $R^C$ and $R^D$ is null; or $R^C$ and $R^D$ are linked to form an optionally substituted $C_3$-$C_8$ ring;

$R^E$ is selected from the group consisting of an optionally substituted aryl and an optionally substituted heteroaryl;

$R^F$ is selected from the group consisting of hydrogen, $C_1$-$C_3$ alkyl, $C_1$-$C_3$ haloalkyl, and an optionally substituted aryl or heteroaryl;

A is selected from the group consisting of an optionally substituted $C_1$-$C_6$ alkyl, an optionally substituted $C_1$-$C_6$ haloalkyl, an optionally substituted $C_1$-$C_6$ heteroalkyl, and $(CH_2)_m R^E$;

E is a monocyclic or bicyclic aromatic ring optionally containing one or more heteroatoms, and optionally fused with a nonaromatic heterocycle or carbocycle;

L is selected from the group consisting of null, $C(R^A)_2$, CO, $CONR^A$, $NR^A CO$, $NR^A CS$, $NR^A C(S)NR^B$ and an optionally substituted $C_1$-$C_6$ heteroalkyl;

X is N or $CR^5$;

Y is selected from the group consisting of a 1-4 atom spacer comprising one or more groups selected from an optionally substituted $C_1$-$C_6$ alkyl, an optionally substituted $C_1$-$C_6$ heteroalkyl, an optionally substituted phenyl, and an optionally substituted heteroaryl;

Z is selected from the group consisting of null, a 2-5 atom spacer selected from an optionally substituted $C_6$-$C_{10}$ aryl and an optionally substituted $C_1$-$C_8$ heteroaryl, and a 1-5 atom spacer of selected from an optionally substituted $C_1$-$C_6$ alkyl, an optionally substituted $C_1$-$C_6$ heteroalkyl, and an optionally substituted $C_1$-$C_6$ haloalkyl; and m is 0, 1, or 2.

Certain embodiments relate to compounds with the following structures:

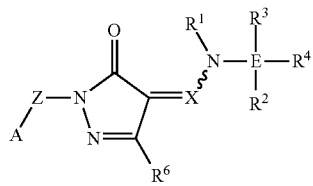

(II)

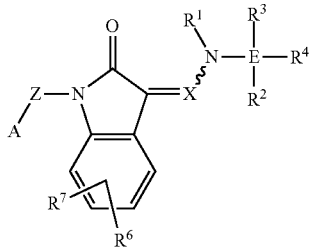

(III)

wherein:

$R^1$ selected from the group consisting of hydrogen, an optionally substituted $C_1$-$C_6$ alkyl, an optionally substituted $C_1$-$C_6$ haloalkyl, and an optionally substituted $C_1$-$C_6$ heteroalkyl;

$R^2$ is selected from the group consisting of hydrogen, halogen, $OR^C$, $NR^C R^D$, $SR^C$, $NO_2$, CN, $(CH_2)_m R^E$, an optionally substituted $C_1$-$C_6$ alkyl, an optionally substituted $C_1$-$C_6$ haloalkyl, and an optionally substituted $C_1$-$C_6$ heteroalkyl; or $R^2$ and $R^1$ are linked to form an optionally substituted $C_5$-$C_8$ ring;

$R^3$ is selected from the group consisting of hydrogen, halogen, $OR^A$, $NR^A R^B$, and $SR^A$; or $R^1$ and $R^2$ are linked to form an optionally substituted heterocycle;

$R^4$ is selected from the group consisting of hydrogen, halogen, an optionally substituted $C_1$-$C_8$ alkyl, an optionally substituted $C_1$-$C_8$ haloalkyl, an optionally substituted $C_1$-$C_8$ heteroalkyl, and $(CH_2)_m R^E$;

$R^5$ selected from the group consisting of hydrogen, an optionally substituted $C_1$-$C_6$ alkyl, an optionally substituted $C_1$-$C_6$ haloalkyl, and an optionally substituted $C_1$-$C_6$ heteroalkyl;

$R^6$ is selected from the group consisting of hydrogen, halogen, $OR^C$, $NR^C R^D$, $NO_2$, CN, $CO_2R^A$, $CONR^C R^D$, $(CH_2)_m R^E$, an optionally substituted $C_1$-$C_6$ alkyl, an optionally substituted $C_1$-$C_6$ haloalkyl, and an optionally substituted $C_1$-$C_6$ heteroalkyl;

$R^7$ is selected from the group consisting of hydrogen, halogen, an optionally substituted $C_1$-$C_6$ alkyl, an optionally substituted $C_1$-$C_6$ haloalkyl, an optionally substituted $C_1$-$C_6$ heteroalkyl, and an optionally substituted aryl or heteroaryl;

$R^A$ is selected from the group consisting of hydrogen, $C_1$-$C_6$ alkyl, $C_1$-$C_6$ haloalkyl, $C_1$-$C_6$ heteroalkyl, and $C_1$-$C_6$ heterohaloalkyl;

$R^B$ is selected from hydrogen, $SO_2R^F$, $COR^F$, $CONR^C R^D$, $C_1$-$C_6$ alkyl, $C_1$-$C_6$ haloalkyl, $C_1$-$C_6$ heteroalkyl, and $C_1$-$C_6$ heterohaloalkyl;

$R^C$ and $R^D$ are each independently selected from the group consisting of hydrogen, an optionally substituted $C_1$-$C_6$ alkyl, an optionally substituted $C_1$-$C_6$ haloalkyl, an optionally substituted $C_1$-$C_6$ heteroalkyl, and $(CH_2)_m R^E$; or one of $R^C$ and $R^D$ is an optionally substituted $C_2$-$C_6$ alkyl and the other of $R^C$ and $R^D$ is null; or $R^C$ and $R^D$ are linked to form an optionally substituted $C_3$-$C_8$ ring;

$R^E$ is selected from an optionally substituted aryl and an optionally substituted heteroaryl;

$R^F$ is selected from the group consisting of hydrogen, $C_1$-$C_3$ alkyl, $C_1$-$C_3$ haloalkyl, and an optionally substituted aryl or heteroaryl;

A is selected from the group consisting of an optionally substituted $C_1$-$C_6$ alkyl, an optionally substituted $C_1$-$C_6$ haloalkyl, an optionally substituted $C_1$-$C_6$ heteroalkyl, and $(CH_2)_m R^E$;

E is a monocyclic or bicyclic aromatic ring optionally containing one or more heteroatoms, and optionally fused with a nonaromatic heterocycle or carbocycle;

X is N or $CR^5$;

Z is selected from the group consisting of null, a 2-5 atom spacer selected from an optionally substituted $C_6$-$C_{10}$ aryl and an optionally substituted $C_1$-$C_8$ heteroaryl, and a 1-5 atom spacer of selected from an optionally substituted $C_1$-$C_6$ alkyl, an optionally substituted $C_1$-$C_6$ heteroalkyl, and an optionally substituted $C_1$-$C_6$ haloalkyl; and m is 0, 1, or 2;

with the proviso that none of $R^2$, $R^3$, and $R^4$ of formula II is —$(CH_2)_{0-6}$—OH when it is at the ortho position;

with the proviso that none of A, Z, $R^2$, $R^3$, and $R^4$ contain a carboxylic acid or carboxylic acid derivative or a carboxylic acid bioisostere.

In certain embodiments, the compounds with the following structures are provided:

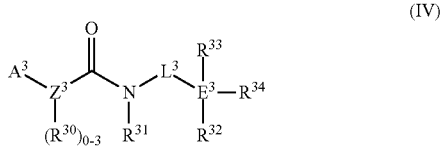

(IV)

wherein:

$R^{30}$ is selected from the group consisting of hydrogen, halogen, $OR^C$, $NR^C R^D$; $SR^C$, $NO_2$, CN, an optionally substituted $C_1$-$C_6$ alkyl, an optionally substituted $C_1$-$C_6$ haloalkyl, and an optionally substituted $C_1$-$C_6$ heteroalkyl;

$R^{31}$ selected from the group consisting of hydrogen, an optionally substituted $C_1$-$C_6$ alkyl, an optionally substituted $C_1$-$C_6$ haloalkyl, and an optionally substituted $C_1$-$C_6$ heteroalkyl;

$R^{32}$ is selected from the group consisting of hydrogen, halogen, $OR^C$, $NR^C R^D$; $SR^C$, $NO_2$, CN, an optionally substituted $C_1$-$C_6$ alkyl, an optionally substituted $C_1$-$C_6$ haloalkyl, and an optionally substituted $C_1$-$C_{10}$ heteroalkyl;

$R^{33}$ is selected from the group consisting of hydrogen, halogen, $OR^A$, $NR^A R^B$, and $SR^A$; or $R^{31}$ and $R^{33}$ are linked to form an optionally substituted heterocycle;

$R^{34}$ is selected from the group consisting of hydrogen, halogen, an optionally substituted $C_1$-$C_8$ alkyl, an optionally substituted $C_1$-$C_8$ haloalkyl, an optionally substituted $C_1$-$C_8$ heteroalkyl, $(CH_2)_m R^E$, and $CH_2 O(CH_2)_m R^E$;

$R^A$ is selected from the group consisting of hydrogen, $C_1$-$C_6$ alkyl, $C_1$-$C_6$ haloalkyl, $C_1$-$C_6$ heteroalkyl, and $C_1$-$C_6$ heterohaloalkyl;

$R^B$ is selected from the group consisting of hydrogen, $SO_2 R^F$, $COR^F$, $CONR^C R^D$, $C_1$-$C_6$ alkyl, $C_1$-$C_6$ haloalkyl, $C_1$-$C_6$ heteroalkyl, and $C_1$-$C_6$ heterohaloalkyl;

$R^C$ and $R^D$ are each independently selected from the group consisting of hydrogen, an optionally substituted $C_1$-$C_6$ alkyl, an optionally substituted $C_1$-$C_6$ haloalkyl, an optionally substituted $C_1$-$C_6$ heteroalkyl, and $(CH_2)_m R^E$; or one of $R^C$ and $R^D$ is an optionally substituted $C_2$-$C_6$ alkyl and the other of $R^C$ and $R^D$ is null; or $R^C$ and $R^D$ are linked to form an optionally substituted $C_3$-$C_8$ ring;

$R^E$ is selected from an optionally substituted aryl and an optionally substituted heteroaryl;

$R^F$ is selected from the group consisting of hydrogen, $C_1$-$C_3$ alkyl, $C_1$-$C_3$ haloalkyl, and an optionally substituted aryl or heteroaryl;

$A^3$ is selected from the group consisting of an optionally substituted $C_1$-$C_6$ alkyl, an optionally substituted $C_1$-$C_6$ haloalkyl, an optionally substituted $C_1$-$C_6$ heteroalkyl, a nonaromatic heterocycle, $OR^C$, $NR^A R^B$, and $(CH_2)_m R^E$;

$E^3$ is a monocyclic or bicyclic aromatic ring optionally containing one or more heteroatoms, and optionally fused with a nonaromatic heterocycle or carbocycle;

$L^3$ is selected from the group consisting of $CR^C R^D$, O, S, $NR^A$, $N=CR^C$, an optionally substituted $C_1$-$C_4$ alkyl, an optionally substituted $C_1$-$C_4$ haloalkyl, and an optionally substituted $C_1$-$C_4$ heteroalkyl; or $L^3$ and $R^{31}$ are linked to form an optionally substituted $C_3$-$C_8$ ring;

$Z^3$ is selected from the group consisting of a $C_6$-$C_{10}$ arylalkyl, a $C_6$-$C_{10}$ arylheteroalkyl, a $C_3$-$C_{10}$ heteroarylalkyl, a $C_3$-$C_{10}$ heteroarylheteroalkyl, and a monocyclic or bicyclic aromatic ring optionally containing one or more heteroatoms and optionally fused with a nonaromatic heterocycle or carbocycle; and m is 0, 1, or 2

Certain compounds of the present embodiments may exist as stereoisomers including optical isomers. The present disclosure is intended to include all stereoisomers and both the racemic mixtures of such stereoisomers as well as the individual enantiomers that may be separated according to methods that are known in the art or that may be excluded by synthesis schemes known in the art designed to yield predominantly one enantiomer relative to another.

Certain Synthesis Methods

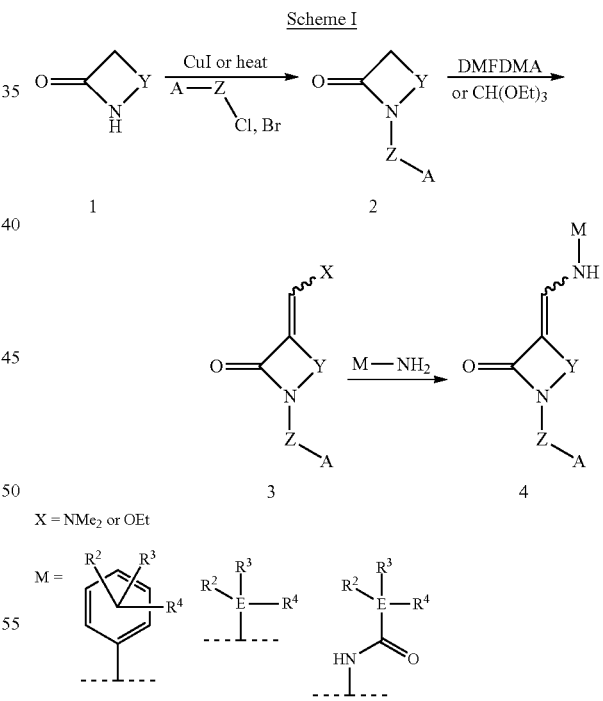

The process of Scheme I is a multi-step synthetic sequence that commences with a metal catalyzed cross-coupling or simple alkylation of a cyclic amide compound such as structure 1 and an aryl or alkyl bromide to provide an N-substituted intermediate of structure 2. This is then converted into the structure 3 via reaction with either dimethylformamide dimethylacetal (or equivalent) or triethylorthoformate. This is then reacted with an amine to give the structure 4.

Scheme II

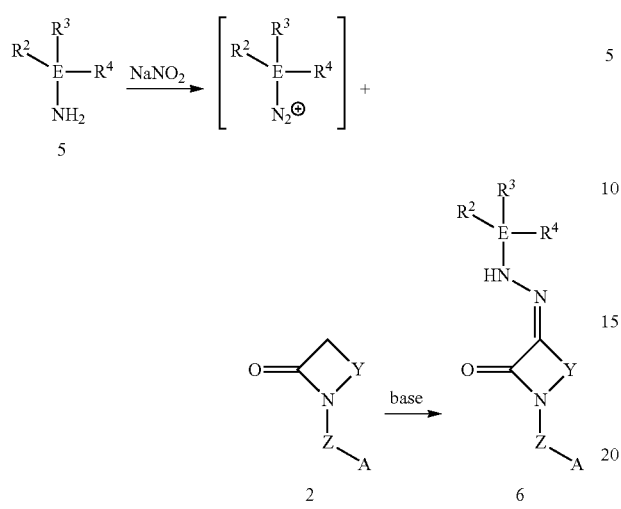

The process of Scheme II is a synthetic sequence that commences with the diazotization of an aromatic primary amine such as structure 5 under standard conditions followed by the treatment of the appropriate coupling partner such as 2 under a basic condition to give the final products of structure 6.

Scheme III

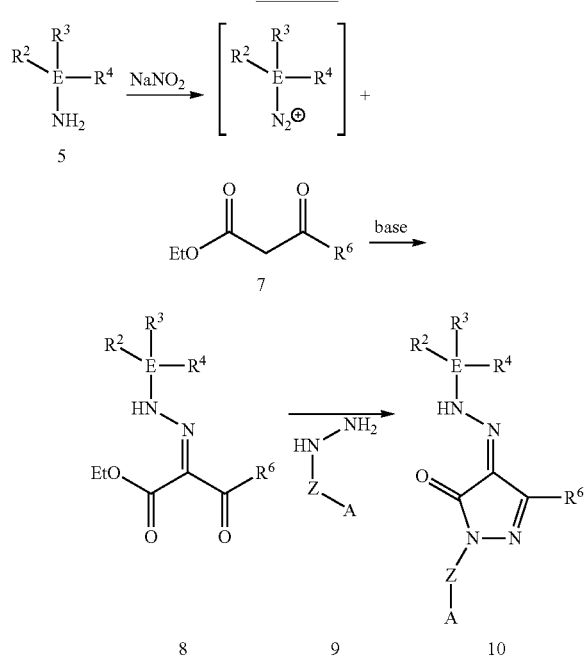

Scheme III describes synthesis of the pyrazolone compounds of structure 10. Diazotization of an aromatic primary amine such as structure 5 under standard conditions followed by the treatment of a ketoester compound of structure 7 under a basic condition gives the intermediates of structure 8. Condensation of compounds of structure 8 and hydrazine derivative 9 affords the final compounds of structure 10.

Scheme IV

Scheme IV describes the synthesis of compounds of structure 14 from a carboxylic acid derivative of structure 11 via a hydrazide intermediate (12) condensation reaction with an aldehyde or a ketone derivative (13).

One of skill in the art will recognize that analogous synthesis schemes may be used to synthesize similar compounds. One of skill will recognize that compounds of the present embodiments may be synthesized using other synthesis schemes. In certain embodiments, a salt corresponding to any of the compounds provided herein is provided.

In certain embodiments, a salt corresponding to a selective HGF modulator is provided. In certain embodiments, a salt corresponding to a selective HGF receptor binding agent is provided. In certain embodiments, a salt is obtained by reacting a compound with an acid, such as hydrochloric acid, hydrobromic acid, sulfuric acid, nitric acid, phosphoric acid, methanesulfonic acid, ethanesulfonic acid, p-toluenesulfonic acid, salicylic acid, and the like. In certain embodiments, a salt is obtained by reacting a compound with a base to form a salt such as an ammonium salt, an alkali metal salt, such as a sodium or a potassium salt, an alkaline earth metal salt, such as a calcium or a magnesium salt, a salt of organic bases such as choline, dicyclohexylamine, N-methyl-D-glucamine, tris (hydroxymethyl)methylamine, 4-(2-hydroxyethyl)-morpholine, 1-(2-hydroxyethyl)-pyrrolidine, ethanolamine and salts with amino acids such as arginine, lysine, and the like. In certain embodiments, a salt is obtained by reacting a free acid form of a selective HGF modulator or selective HGF binding agent with multiple molar equivalents of a base, such as bis-sodium, bis-ethanolamine, and the like.

In certain embodiments, a salt corresponding to a compound of the present embodiments is selected from acetate, ammonium, benzenesulfonate, benzoate, bicarbonate, bisulfate, bitartrate, borate, bromide, calcium edetate, camsylate, carbonate, chloride, cholinate, clavulanate, citrate, dihydrochloride, diphosphate, edetate, edisylate, estolate, esylate, fumarate, gluceptate, gluconate, glutamate, glycollylarsanilate, hexylresorcinate, hydrabanine, hydrobromide, hydrochloride, hydroxynaphthoate, iodide, isethionate, lactate, lactobionate, laurate, magnesium, malate, maleate, mandelate, mucate, napsylate, nitrate, N-methylglucamine, oxalate, pamoate (embonate), palmitate, pantothenate, phosphate, polygalacturonate, potassium, salicylate, sodium, stearate, subaceatate, succinate, sulfate, tannate, tartrate, teoclate, tosylate, triethiodide, tromethamine, trimethylammonium, and valerate salts.

In certain embodiments, one or more carbon atoms of a compound of the present embodiments are replaced with silicon. See e.g., WO 03/037905A1; Tacke and Zilch, Endeavour, New Series, 10, 191-197 (1986); Bains and Tacke, Curr. Opin. Drug Discov Devel. July: 6(4):526-43 (2003), all of which are incorporated herein by reference in their entirety. In certain embodiments, compounds comprising one or more silicon atoms possess certain desired properties, including, but not limited to, greater stability and/or longer half-life in a patient, when compared to the same compound in which none of the carbon atoms have been replaced with a silicon atom.

Certain Assays

In certain embodiments, assays may be used to determine the level of HGF modulating activity of the compounds of the present embodiments.

Proliferation Assay

In some embodiments, compounds are tested in an in vitro proliferation assay using the cell lines that express EPO, TPO, GCSF or other cytokine receptors that may be dependant upon these cytokines for their growth.

Luciferase Assay

In some embodiments, compounds are tested in a reporter assay using the cell lines that express EPO, TPO, GCSF or other cytokine receptors. These cells are transfected with the STAT responsive reporter (such as luciferase) and the activity of the compounds is determined by a reporter assay.

Differentiation Assay

In some embodiments, compounds are tested in purified human CD34+ progenitor cells. After addition of the compounds to the cells, the number of cells expressing markers of hematopoiesis, erythropoiesis, granulopoiesis, thrombopoiesis, or myelopoiesis is measured by flow cytometry or by analyzing expression of genes associated with these pathways.

Certain Pharmaceutical Agents

In certain embodiments, at least one selective HGF modulator, or pharmaceutically acceptable salt, ester, amide, and/or prodrug thereof, either alone or combined with one or more pharmaceutically acceptable carriers, forms a pharmaceutical agent. Techniques for formulation and administration of compounds of the present embodiments may be found for example, in "Remington's Pharmaceutical Sciences," Mack Publishing Co., Easton, Pa., 18th edition, 1990, which is incorporated herein by reference in its entirety.

In certain embodiments, a pharmaceutical agent comprising one or more compounds of the present embodiments is prepared using known techniques, including, but not limited to mixing, dissolving, granulating, dragee-making, levigating, emulsifying, encapsulating, entrapping or tabletting processes.

In certain embodiments, a pharmaceutical agent comprising one or more compounds of the present embodiments is a liquid (e.g., a suspension, elixir and/or solution). In certain of such embodiments, a liquid pharmaceutical agent comprising one or more compounds of the present embodiments is prepared using ingredients known in the art, including, but not limited to, water, glycols, oils, alcohols, flavoring agents, preservatives, and coloring agents.

In certain embodiments, a pharmaceutical agent comprising one or more compounds of the present embodiments is a solid (e.g., a powder, tablet, and/or capsule). In certain of such embodiments, a solid pharmaceutical agent comprising one or more compounds of the present embodiments is prepared using ingredients known in the art, including, but not limited to, starches, sugars, diluents, granulating agents, lubricants, binders, and disintegrating agents.

In certain embodiments, a pharmaceutical agent comprising one or more compounds of the present embodiments is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical agent comprising one or more compounds of the present embodiments comprises a delivery system. Examples of delivery systems include, but are not limited to, liposomes and emulsions. Certain delivery systems are useful for preparing certain pharmaceutical agents including those comprising hydrophobic compounds. In certain embodiments, certain organic solvents such as dimethylsulfoxide are used.

In certain embodiments, a pharmaceutical agent comprising one or more compounds of the present embodiments comprises one or more tissue-specific delivery molecules designed to deliver the pharmaceutical agent to specific tissues or cell types. For example, in certain embodiments, pharmaceutical agents include liposomes coated with a tissue-specific antibody.

In certain embodiments, a pharmaceutical agent comprising one or more compounds of the present embodiments comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™, and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical agent comprising one or more compounds of the present embodiments comprises a sustained-release system. A non-limiting example of such a sustained-release system is a semi-permeable matrix of solid hydrophobic polymers. In certain embodiments, sustained-release systems may, depending on their chemical nature, release compounds over a period of hours, days, weeks or months.

Certain compounds used in pharmaceutical agent of the present embodiments may be provided as pharmaceutically acceptable salts with pharmaceutically compatible counterions. Pharmaceutically compatible salts may be formed with many acids, including but not limited to hydrochloric, sulfuric, acetic, lactic, tartaric, malic, succinic, etc.

In certain embodiments, a pharmaceutical agent comprising one or more compounds of the present embodiments comprises an active ingredient in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, a pharmaceutical agent comprising one or more compounds of the present embodiments is formulated as a prodrug. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, a prodrug is an ester. In certain embodiments, such prodrugs are less water soluble than the corresponding active form. In certain instances, such prodrugs possess superior transmittal across cell membranes, where water solubility is detrimental to mobility. In certain embodiments, the ester in such prodrugs is metabolically hydrolyzed to carboxylic acid. In certain instances the carboxylic acid containing compound is the corresponding active form. In certain embodiments, a prodrug comprises a short peptide (polyaminoacid) bound to an acid group. In certain of such embodiments, the peptide is metabolized to form the corresponding active form.

In certain embodiments, a pharmaceutical agent comprising one or more compounds of the present embodiments is useful for treating a conditions or disorder in a mammalian, and particularly in a human patient. Suitable administration routes include, but are not limited to, oral, rectal, transmucosal, intestinal, enteral, topical, suppository, through inhalation, intrathecal, intraventricular, intraperitoneal, intranasal, intraocular and parenteral (e.g., intravenous, intramuscular, intramedullary, and subcutaneous). In certain embodiments, pharmaceutical intrathecals are administered to achieve local rather than systemic exposures. For example, pharmaceutical agents may be injected directly in the area of desired effect (e.g., in the renal or cardiac area).

In certain embodiments, a pharmaceutical agent comprising one or more compounds of the present embodiments is administered in the form of a dosage unit (e.g., tablet, capsule, bolus, etc.). In certain embodiments, such dosage units comprise a selective HGF modulator in a dose from about 1 µg/kg of body weight to about 50 mg/kg of body weight. In certain embodiments, such dosage units comprise a selective HGF modulator in a dose from about 2 µg/kg of body weight to about 25 mg/kg of body weight. In certain embodiments, such dosage units comprise a selective HGF modulator in a dose from about 10 µg/kg of body weight to about 5 mg/kg of body weight. In certain embodiments, pharmaceutical agents are administered as needed, once per day, twice per day, three times per day, or four or more times per day. It is recognized by those skilled in the art that the particular dose, frequency, and duration of administration depends on a number of factors, including, without limitation, the biological activity desired, the condition of the patient, and tolerance for the pharmaceutical agent.

In certain embodiments, a pharmaceutical agent comprising a compound of the present embodiments is prepared for oral administration. In certain of such embodiments, a pharmaceutical agent is formulated by combining one or more compounds of the present embodiments with one or more pharmaceutically acceptable carriers. Certain of such carriers enable compounds of the present embodiments to be formulated as tablets, pills, dragees, capsules, liquids, gels, syrups, slurries, suspensions and the like, for oral ingestion by a patient. In certain embodiments, pharmaceutical agents for oral use are obtained by mixing one or more compounds of the present embodiments and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical agents are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain of such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical agents for oral administration are push-fit capsules made of gelatin. Certain of such push-fit capsules comprise one or more compounds of the present embodiments in admixture with one or more filler such as lactose, binders such as starches, and/or lubricants such as talc or magnesium stearate and, optionally, stabilizers. In certain embodiments, pharmaceutical agents for oral administration are soft, sealed capsules made of gelatin and a plasticizer, such as glycerol or sorbitol. In certain soft capsules, one or more compounds of the present embodiments are be dissolved or suspended in suitable liquids, such as fatty oils, liquid paraffin, or liquid polyethylene glycols. In addition, stabilizers may be added.

In certain embodiments, pharmaceutical agents are prepared for buccal administration. Certain of such pharmaceutical agents are tablets or lozenges formulated in conventional manner.

In certain embodiments, a pharmaceutical agent is prepared for administration by injection (e.g., intravenous, subcutaneous, intramuscular, etc.). In certain of such embodiments, a pharmaceutical agent comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical agents for injection are presented in unit dosage form, e.g., in ampoules or in multi-dose containers. Certain pharmaceutical agents for injection are suspensions, solutions or emulsions in oily or aqueous vehicles, and may contain formulatory agents such as suspending, stabilizing and/or dispersing agents. Certain solvents suitable for use in pharmaceutical agents for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the compounds to allow for the preparation of highly concentrated solutions.

In certain embodiments, a pharmaceutical agent is prepared for transmucosal administration. In certain of such embodiments penetrants appropriate to the barrier to be permeated are used in the formulation. Such penetrants are generally known in the art.

In certain embodiments, a pharmaceutical agent is prepared for administration by inhalation. Certain of such pharmaceutical agents for inhalation are prepared in the form of an aerosol spray in a pressurized pack or a nebulizer. Certain of such pharmaceutical agents comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a compound of the present embodiments and a suitable powder base such as lactose or starch.

In certain embodiments, a pharmaceutical agent is prepared for rectal administration, such as a suppositories or retention enema. Certain of such pharmaceutical agents comprise known ingredients, such as cocoa butter and/or other glycerides.

In certain embodiments, a pharmaceutical agent is prepared for topical administration. Certain of such pharmaceutical agents comprise bland moisturizing bases, such as ointments or creams. Exemplary suitable ointment bases include, but are not limited to, petrolatum, petrolatum plus volatile silicones, lanolin and water in oil emulsions such as Eucerin™, available from Beiersdorf (Cincinnati, Ohio). Exemplary suitable cream bases include, but are not limited to, Nivea™ Cream, available from Beiersdorf (Cincinnati, Ohio), cold cream (USP), Purpose Cream™, available from Johnson & Johnson (New Brunswick, N.J.), hydrophilic ointment (USP) and Lubriderm™, available from Pfizer (Morris Plains, N.J.).

In certain embodiments, the formulation, route of administration and dosage for a pharmaceutical agent of the present embodiments can be chosen in view of a particular patient's condition. (See e.g., Fingl et al. 1975, in "The Pharmacological Basis of Therapeutics", Ch. 1 p. 1, which is incorporated herein by reference in its entirety). In certain embodiments, a pharmaceutical agent is administered as a single dose. In certain embodiments, a pharmaceutical agent is administered as a series of two or more doses administered over one or more days.

In certain embodiments, a pharmaceutical agent of the present embodiments is administered to a patient between about 0.1% and 500%, 5% and 200%, 10% and 100%, 15% and 85%, 25% and 75%, or 40% and 60% of an established human dosage. Where no human dosage is established, a suitable human dosage may be inferred from $ED_{50}$ or $ID_{50}$ values, or other appropriate values derived from in vitro or in vivo studies.

In certain embodiments, a daily dosage regimen for a patient comprises an oral dose of between 0.1 mg and 2000 mg, 5 mg and 1500 mg, 10 mg and 1000 mg, 20 mg and 500 mg, 30 mg and 200 mg, or 40 mg and 100 mg of a compound of the present embodiments. In certain embodiments, a daily dosage regimen is administered as a single daily dose. In certain embodiments, a daily dosage regimen is administered as two, three, four, or more than four doses.

In certain embodiments, a pharmaceutical agent of the present embodiments is administered by continuous intravenous infusion. In certain of such embodiments, from 0.1 mg to 500 mg of a composition of the present embodiments is administered per day.

In certain embodiments, a pharmaceutical agent of the present embodiments is administered for a period of continuous therapy. For example, a pharmaceutical agent of the present embodiments may be administered over a period of days, weeks, months, or years.

Dosage amount, interval between doses, and duration of treatment may be adjusted to achieve a desired effect. In certain embodiments, dosage amount and interval between doses are adjusted to maintain a desired concentration on compound in a patient. For example, in certain embodiments, dosage amount and interval between doses are adjusted to provide plasma concentration of a compound of the present embodiments at an amount sufficient to achieve a desired effect. In certain of such embodiments the plasma concentration is maintained above the minimal effective concentration (MEC). In certain embodiments, pharmaceutical agents of the present embodiments are administered with a dosage regimen designed to maintain a concentration above the MEC for 10-90% of the time, between 30-90% of the time, or between 50-90% of the time.

In certain embodiments in which a pharmaceutical agent is administered locally, the dosage regimen is adjusted to achieve a desired local concentration of a compound of the present embodiments.

In certain embodiments, a pharmaceutical agent may be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the present embodiments formulated in a compatible pharmaceutical carrier may also be prepared, placed in an appropriate container, and labeled for treatment of an indicated condition.

In certain embodiments, a pharmaceutical agent is in powder form for constitution with a suitable vehicle, e.g., sterile pyrogen-free water, before use.

Certain Combination Therapies

In certain embodiments, one or more pharmaceutical agents of the present embodiments are co-administered with one or more other pharmaceutical agents. In certain embodiments, such one or more other pharmaceutical agents are designed to treat the same disease or condition as the one or more pharmaceutical agents of the present embodiments. In certain embodiments, such one or more other pharmaceutical agents are designed to treat a different disease or condition as the one or more pharmaceutical agents of the present embodiments. In certain embodiments, such one or more other pharmaceutical agents are designed to treat an undesired effect of one or more pharmaceutical agents of the present embodiments. In certain embodiments, one or more pharmaceutical agents of the present embodiments are co-administered with another pharmaceutical agent to treat an undesired effect of that other pharmaceutical agent. In certain embodiments, one or more pharmaceutical agents of the present embodiments and one or more other pharmaceutical agents are administered at the same time. In certain embodiments, one or more pharmaceutical agents of the present embodiments and one or more other pharmaceutical agents are administered at the different times. In certain embodiments, one or more pharmaceutical agents of the present embodiments and one or more other pharmaceutical agents are prepared together in a single formulation. In certain embodiments, one or more pharmaceutical agents of the present embodiments and one or more other pharmaceutical agents are prepared separately.

Examples of pharmaceutical agents that may be co-administered with a pharmaceutical agent of the present embodiments include, but are not limited to, anti-cancer treatments, including, but not limited to, chemotherapy and radiation treatment; corticosteroids, including but not limited to prednisone; immunoglobulins, including, but not limited to intravenous immunoglobulin (IVIg); analgesics (e.g., acetaminophen); anti-inflammatory agents, including, but not limited to non-steroidal anti-inflammatory drugs (e.g., ibuprofen, COX-1 inhibitors, and COX-2, inhibitors); salicylates; antibiotics; antivirals; antifungal agents; antidiabetic agents (e.g., biguanides, glucosidase inhibitors, insulins, sulfonylureas, and thiazolidenediones); adrenergic modifiers; diuretics; hormones (e.g., anabolic steroids, androgen, estrogen, calcitonin, progestin, somatostan, and thyroid hormones); immunomodulators; muscle relaxants; antihistamines; osteoporosis agents (e.g., biphosphonates, calcitonin, and estrogens); prostaglandins, antineoplastic agents; psychotherapeutic agents; sedatives; poison oak or poison sumac products; antibodies; and vaccines.

Certain Indications

In certain embodiments, provided are methods of treating a patient comprising administering one or more compounds of the present embodiments. In certain embodiments, such patient suffers from thrombocytopenia. In certain such embodiments, thrombocytopenia results from chemotherapy and/or radiation treatment. In certain embodiments, thrombocytopenia results bone marrow failure resulting from bone marrow transplantation and/or aplastic anemia. In certain embodiments thrombocytopenia is idiopathic. In certain embodiments, one or more compounds of the present embodiments are administered to a patient to in conjunction with harvesting peripheral blood progenitor cells and/or in conjunction with platelet apheresis. Such administration may be done before, during, and/or after such harvesting.

In certain embodiments, one or more compounds of the present embodiments are administered to a patient who suffers from a condition affecting the nervous system, including, but are not limited to, diseases affecting the nervous system and injuries to the nervous system. Such diseases, include, but not limited to, amyotrophic lateral sclerosis, multiple sclerosis, and multiple dystrophy. Injury to the nervous system include, but are not limited to spinal cord injury or peripheral nerve damage, including, but not limited to, injury resulting from trauma or from stroke. In certain embodiments, one or more compounds of the present embodiments are used to promote growth and/or development of glial cells. Such glial cells may repair nerve cells. In certain embodiments, compounds of the present embodiments are used to treat psychological disorders, including, but not limited to, cognitive disorders.

EXAMPLES

The following examples are set forth merely to assist in understanding the embodiments and should not be construed as limiting the embodiments described and claimed herein in any way. Variations of the invention, including the substitution of all equivalents now known or later developed, which would be within the purview of those skilled in the art, and changes in formulation or minor changes in experimental design, are to be considered to fall within the scope of the invention incorporated herein.

Example 1

4-(4-Hydroxyphenyl)hydrazono-1-(4-phenylthiazolyl-2)-3-methyl-5-pyrazolone (Compound 101)

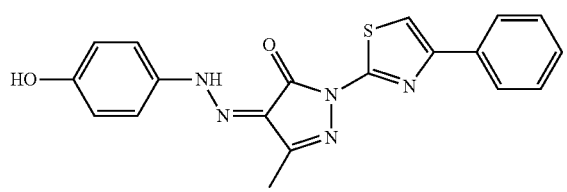 [SMILES: CC1=NN(c2nc(-c3ccccc3)cs2)C(=O)/C1=N\Nc1ccc(O)cc1]

Compound 101 above was prepared according to the procedure described in Scheme IV above from 4-hydroxyaniline and (4-phenylthiazolyl-2)-5-pyrazolone. The molecular weight for $C_{19}H_{15}N_5O_2S$ is 377.42; m/z 378.02 (MH$^+$).

Example 2

4-(4-Hydroxyphenyl)hydrazono-1-(2-pyridyl)-3-methyl-5-pyrazolone (Compound 102)

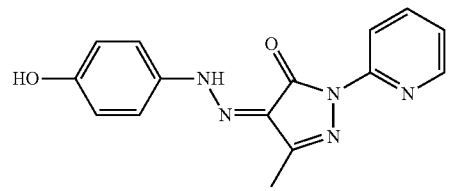 [SMILES: CC1=NN(c2ccccn2)C(=O)/C1=N\Nc1ccc(O)cc1]

Compound 102 above was prepared according to the procedure described in Scheme III above from 4-hydroxyaniline and 2-pyridylhydrazine. The molecular weight of $C_{15}H_{13}N_5O_2$ is 295.30; m/z (MH$^+$): calculated 296.11 and observed 296.10.

Example 3

4-(4-Hydroxyphenyl)hydrazono-1-(5-methyl-2-pyridyl)-3-methyl-5-pyrazolone (Compound 103)

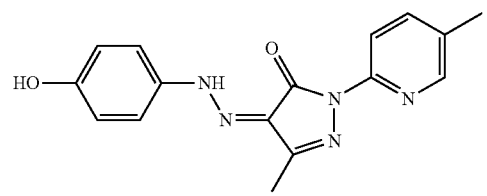 [SMILES: CC1=NN(c2ccc(C)cn2)C(=O)/C1=N\Nc1ccc(O)cc1]

Compound 103 above was prepared according to the procedure described in Scheme III above from 4-hydroxyaniline and 5-methyl-2-pyridylhydrazine. The molecular weight of $C_{16}H_{15}N_5O_2$: is 309.32; m/z (MH+): calculated 310.13 and observed 310.09.

Example 4

4-(4-Hydroxyphenyl)hydrazono-1-(4-(4-methylphenyl)thiazolyl-2)-3-methyl-5-pyrazolone (Compound 104)

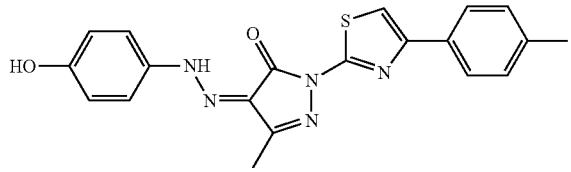 [SMILES: CC1=NN(c2nc(-c3ccc(C)cc3)cs2)C(=O)/C1=N\Nc1ccc(O)cc1]

Compound 104 above was prepared according to the procedure described in Scheme IV above from 4-hydroxyaniline and (4-(4-methylphenyl)thiazolyl-2)-5-pyrazolone. The molecular weight of $C_{20}H_{17}N_5O_2S$: 391.45 is m/z (MH+): calculated 392.11 and observed 392.04.

Example 5

4-(4-Hydroxyphenyl)hydrazono-1-(4-(3-methoxyphenyl)thiazolyl-2)-3-methyl-5-pyrazolone (Compound 105)

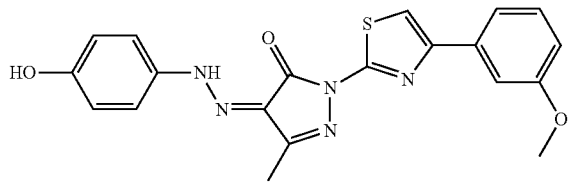 [SMILES: COc1cccc(-c2csc(N3N=C(C)/C(=N/Nc4ccc(O)cc4)C3=O)n2)c1]

Compound 105 above was prepared according to the procedure described in Scheme IV above from 4-hydroxyaniline and (4-(3-methoxyphenyl)thiazolyl-2)-5-pyrazolone. The molecular weight of $C_{20}H_{17}N_5O_3S$ is 407.45; m/z (MH+): calculated 408.11 and observed 408.03.

Example 6

4-(4-Hydroxyphenyl)hydrazono-1-(4-(3-methylphenyl)thiazolyl-2)-3-methyl-5-pyrazolone (Compound 106)

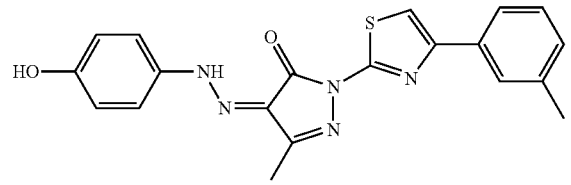 [SMILES: CC1=NN(c2nc(-c3cccc(C)c3)cs2)C(=O)/C1=N\Nc1ccc(O)cc1]

Compound 106 above was prepared according to the procedure described in Scheme IV above from 4-hydroxyaniline and (4-(3-methylphenyl)thiazolyl-2)-5-pyrazolone. $^1$H NMR (500 MHz, CD$_3$OD) 7.84 (s, 1H), 7.76 (d, 1H), 7.50 (s, 1H), 7.46 (d, 2H), 7.29 (t, 1H), 7.15 (d, 1H), 6.89 (d, 2H), and 2.41 (s, 6H).

Example 7

4-(4-Hydroxyphenyl)hydrazono-1-(4-(2-methylphenyl)thiazolyl-2)-3-methyl-5-pyrazolone (Compound 107)

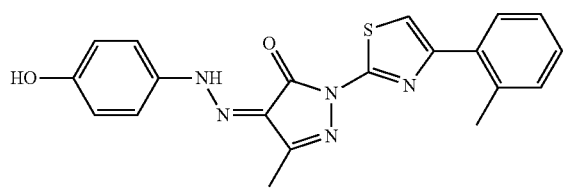 [SMILES: CC1=NN(c2nc(-c3ccccc3C)cs2)C(=O)/C1=N\Nc1ccc(O)cc1]

Compound 107 above was prepared according to the procedure described in Scheme IV above from 4-hydroxyaniline and (4-(2-methylphenyl)thiazolyl-2)-5-pyrazolone. The molecular weight of $C_{20}H_{17}N_5O_2S$ is 391.45; m/z (MH+): calculated 392.11 and observed 392.04.

Example 8

4-(4-Hydroxyphenyl)hydrazono-1-(2-quinolino)-3-methyl-5-pyrazolone (Compound 108)

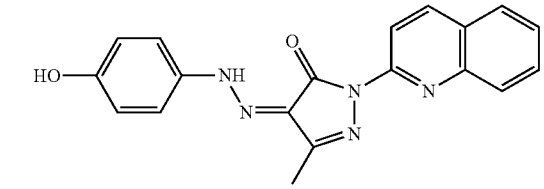 [SMILES: CC1=NN(c2ccc3ccccc3n2)C(=O)/C1=N\Nc1ccc(O)cc1]

Compound 108 above was prepared according to the procedure described in Scheme III above from 4-hydroxyaniline and 2-quinolinohydrazine. $^1$H NMR (500 MHz, CD$_3$OD) 8.40 (d, 1H), 8.33 (d, 1H), 8.08 (d, 1H), 7.91 (d, 1H), 7.75 (t, 1H), 7.56 (t, 1H), 7.46 (d, 2H), 6.90 (d, 2H), and 2.43 (s, 3H).

Example 9

4-(4-Hydroxyphenyl)hydrazono-1-(4-(2-methoxyphenyl)thiazolyl-2)-3-methyl-5-pyrazolone (Compound 109)

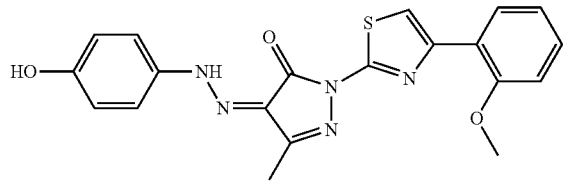 [SMILES: COc1ccccc1-c1csc(N2N=C(C)/C(=N/Nc3ccc(O)cc3)C2=O)n1]

Compound 109 above was prepared according to the procedure described in Scheme IV above from 4-hydroxyaniline and (4-(2-methoxyphenyl)thiazolyl-2)-5-pyrazolone. The $^1$H NMR spectrum (500 MHz, CDCl$_3$) 8.38 (dd, 1H), 7.80 (s, 1H), 7.39 (d, 2H), 7.30 (t, 1H), 7.06 (t, 1H), 6.99 (d, 1H), 6.93 (d, 2H), 3.98 (s, 3H), and 2.47 (s, 3H).

Example 10

4-(4-Hydroxyphenyl)hydrazono-1-(4-methylquinolino-2)-3-methyl-5-pyrazolone (Compound 110)

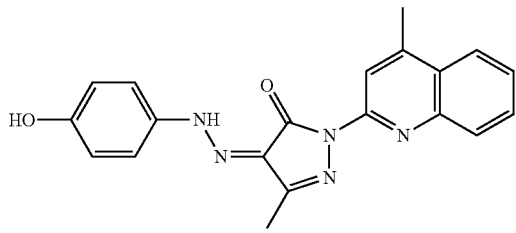 [SMILES: CC1=NN(c2cc(C)c3ccccc3n2)C(=O)/C1=N\Nc1ccc(O)cc1]

Compound 110 above was prepared according to the procedure described in Scheme III above from 4-hydroxyaniline and 2-(4-methylquinolino)hydrazine. The molecular weight of C$_{20}$H$_{17}$N$_5$O$_2$ is 359.38; m/z (MH$^+$): calculated 360.14 and observed 360.07.

Example 11

4-(4-Hydroxyphenyl)hydrazono-1-(4-(2-methoxyphenyl)thiazolyl-2)-3-methyl-5-pyrazolone (Compound III)

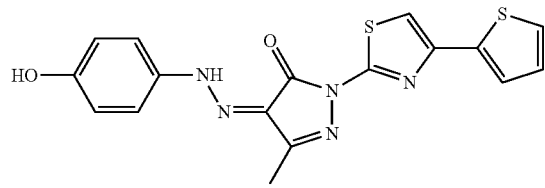 [SMILES: CC1=NN(c2nc(-c3cccs3)cs2)C(=O)/C1=N\Nc1ccc(O)cc1]

Compound III above was prepared according to the procedure described in Scheme IV above from 4-hydroxyaniline and (4-(2-methoxyphenyl)thiazolyl-2)-5-pyrazolone. The molecular weight of C$_{17}$H$_{13}$N$_5$O$_2$S$_2$ is 383.45; m/z (MH$^+$): calculated 384.05 and observed 384.01.

Example 12

4-(4-Hydroxy-3-methoxyphenyl)hydrazono-1-(4-(4-methylphenyl)thiazolyl-2)-3-methyl-5-pyrazolone (Compound 112)

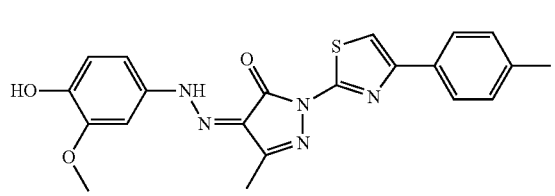 [SMILES: COc1cc(N/N=C2\C(=O)N(c3nc(-c4ccc(C)cc4)cs3)N=C2C)ccc1O]

Compound 112 above was prepared according to the procedure described in Scheme IV above from 4-hydroxy-3-methoxyaniline and (4-(4-methylphenyl)thiazolyl-2)-5-pyrazolone. The molecular weight of C$_{21}$H$_{12}$N$_5$O$_3$S is 421.47; m/z (MH$^+$): calculated 422.12 and observed 421.99.

Example 13

4-(4-Hydroxy-3-methylphenyl)hydrazono-1-(4-(4-methylphenyl)thiazolyl-2)-3-methyl-5-pyrazolone (Compound 113)

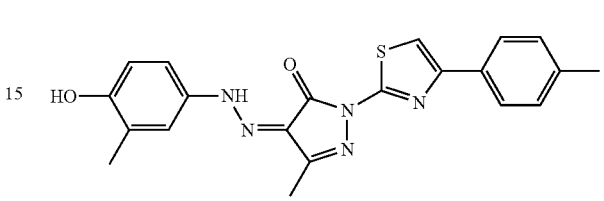

Compound 113 above was prepared according to the procedure described in Scheme IV above from 4-hydroxy-3-methylaniline and (4-(4-methylphenyl)thiazolyl-2)-5-pyrazolone. The molecular weight of C$_{21}$H$_{12}$N$_5$O$_2$S is 405.47; m/z (MH$^+$): calculated 406.13 and observed 406.

Example 14

4-(3-Amino-4-hydroxyphenyl)hydrazono-1-phenyl-3-methyl-5-pyrazolone (Compound 114)

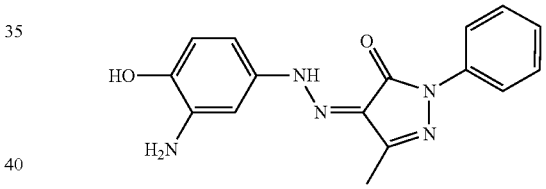

Compound 114 above was prepared according to the procedure described in Scheme III above from 3-amino-4-hydroxyaniline and phenylhydrazine. The molecular weight of C$_{16}$H$_{15}$N$_5$O$_2$ is 309.32; m/z (MH$^+$): calculated 310.13 and observed 310.05.

Example 15

4-(4-Hydroxyphenyl)hydrazono-1-(3-methyl)phenyl-3-methyl-5-pyrazolone (Compound 115)

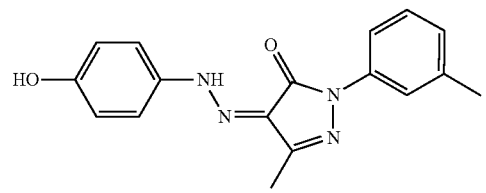 [SMILES: CC1=NN(c2cccc(C)c2)C(=O)/C1=N\Nc1ccc(O)cc1]

Compound 115 above was prepared according to the procedure described in Scheme III above from 4-hydroxyaniline and 3-methylphenylhydrazine. $^1$H NMR (CDCl$_3$, 300 MHz)

7.89 (d, 2H), 7.76-7.64 (m 2H), 7.36-7.29 (m, 1H), 7.05 (d, 1H), 6.91 (d, 2H), 5.49 (br s, 1H), 2.39 (s, 3H), 2.32 (s, 3H).

Example 16

4-(4-Hydroxyphenyl)hydrazono-1-(3-ethyl)phenyl-3-methyl-5-pyrazolone (Compound 116)

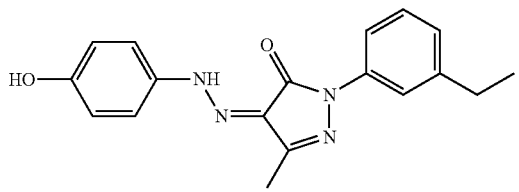 [SMILES: CCc1cccc(N2N=C(C)/C(=N/Nc3ccc(O)cc3)C2=O)c1]

Compound 116 above was prepared according to the procedure described in Scheme III above from 4-hydroxyaniline and 3-ethylphenylhydrazine. The molecular weight of $C_{18}H_{18}N_4O_2$ is 322.36; m/z (MH$^+$): calculated 423.14 and observed 423.14.

Example 17

4-(4-Hydroxyphenyl)hydrazono-1-(5-indanyl)-3-methyl-5-pyrazolone (Compound 117)

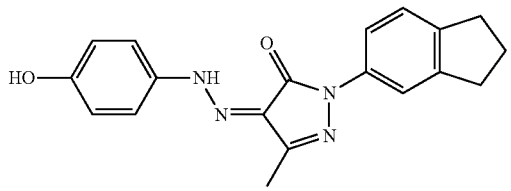 [SMILES: CC1=NN(c2ccc3c(c2)CCC3)C(=O)/C1=N\Nc1ccc(O)cc1]

Compound 117 above was prepared according to the procedure described in Scheme III above from 4-hydroxyaniline and 5-indanylhydrazine. $^1$H NMR (CDCl$_3$, 300 MHz) 7.76 (br s, 1H), 7.67 (d, 1H), 7.35 (d, 1H), 6.93 (d, 2H), 5.07 (br s, 1H), 2.97-2.88 (m, 4H), 2.35 (s, 3H), 2.12-2.07 (m, 2H).

Example 18

4-(4-Hydroxyphenyl)hydrazono-1-(4-methyl-2-pyridyl)-3-methyl-5-pyrazolone (Compound 118)

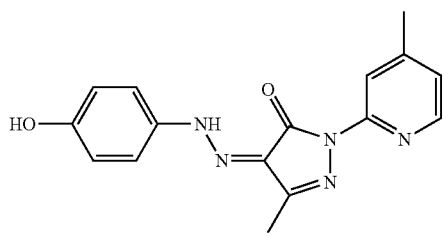 [SMILES: CC1=NN(c2cc(C)ccn2)C(=O)/C1=N\Nc1ccc(O)cc1]

Compound 118 above was prepared according to the procedure described in Scheme III above from 4-hydroxyaniline and 4-methyl-2-pyridylhydrazine. $^1$H NMR (500 MHz, DMSO) 8.30 (d, 1H), 7.72 (s, 1H), 7.45 (d, 2H), 7.10 (d, 1H), 6.84 (d, 2H), 2.36 (s, 3H), 2.27 (s, 3H).

Example 19

6-Fluoro-3-(4-hydroxyphenyl)hydrazono-1-(6-methyl-2-pyridyl)oxindole (Compound 119)

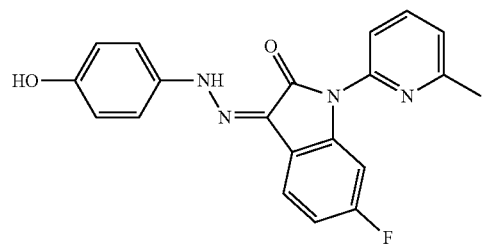 [SMILES: Cc1cccc(N2C(=O)/C(=N\Nc3ccc(O)cc3)c3ccc(F)cc32)n1]

Compound 119 above was prepared according to the procedure described in Scheme II from 4-hydroxyaniline and 5-fluoro-1-(6-methylpyridinyl)oxindole. $^1$H NMR (DMSO, 500 MHz) 12.64 (s), 9.40 (s), 7.91 (t), 7.68 (d), 7.29 (d), and 2.57 (s).

Example 20

6-Fluoro-3-(4-hydroxyphenyl)hydrazono-1-(3-methylphenyl)oxindole (Compound 120)

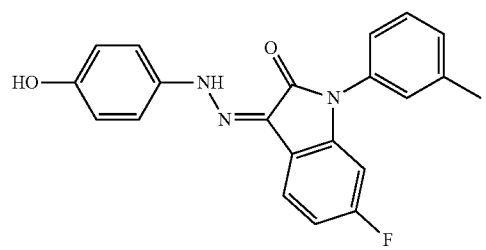 [SMILES: Cc1cccc(N2C(=O)/C(=N\Nc3ccc(O)cc3)c3ccc(F)cc32)c1]

Compound 120 above was prepared according to the procedure described in Scheme II from 4-hydroxyaniline and 5-fluoro-1-(3-methylphenyl)oxindole. $^1$H NMR (CDCl$_3$, 500 MHz) 12.81 (s), 5.05 (s), and 2.42 (s).

Example 21

(1-Methyl-5-methoxyindole-2-)carboxyl(4-hydroxybenzylidene)hydrazide (Compound 121)

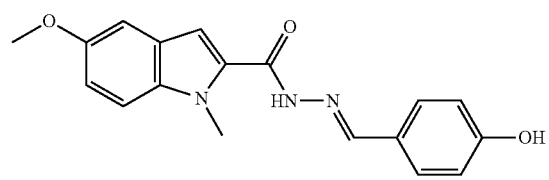 [SMILES: COc1ccc2c(c1)cc(C(=O)N/N=C/c1ccc(O)cc1)n2C]

Compound 121 above was prepared according to the procedure described in Scheme VI above from 4-hydroxybenzaldehyde and 1-methyl-5-methoxyindole-2-carboxylic acid. The molecular weight of $C_{18}H_{17}N_3O_3$ is 323.35; m/z 324.13 (MH$^+$).

Example 22

4-(2-Oxopyrrolidino-1-)benz(3-methoxybenzylidene)hydrazide (Compound 122)

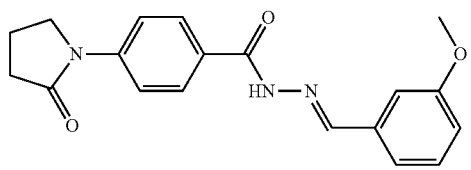 [SMILES: COc1cccc(/C=N/NC(=O)c2ccc(N3CCCC3=O)cc2)c1]

Compound 122 above was prepared according to the procedure described in Scheme VI above from 3-methoxybenzaldehyde and 4-(2-oxopyrrolidino-1-)benzoic acid. The molecular weight of $C_{19}H_{19}N_3O_3$ is 337.37; m/z 338.15 (MH$^+$).

Example 23

4-(2-Oxopyrrolidino-1-)benz(2-hydroxybenzylidene)hydrazide (Compound 123)

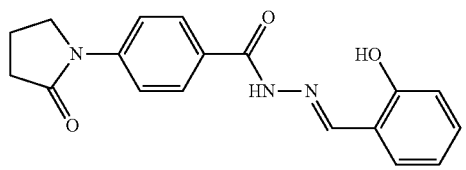 [SMILES: O=C(N/N=C/c1ccccc1O)c1ccc(N2CCCC2=O)cc1]

Compound 123 above was prepared according to the procedure described in Scheme VI above from 2-hydroxybenzaldehyde and 4-(2-oxopyrrolidino-1-)benzoic acid. The molecular weight of $C_{18}H_{17}N_3O_3$ is 323.35; m/z 324.13 (MH$^+$).

Example 24

3-Methylbenz(2-hydroxybenzylidene)hydrazide (Compound 124)

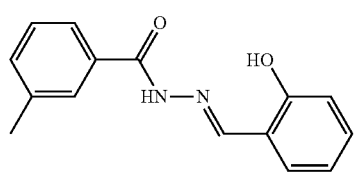 [SMILES: Cc1cccc(C(=O)N/N=C/c2ccccc2O)c1]

Compound 124 above was prepared according to the procedure described in Scheme VI above from 2-hydroxybenzaldehyde and 3-methylbenzoic acid. The molecular weight of $C_{15}H_{14}N_2O_2$ is 254.28; m/z 255.11 (MH$^+$).

Example 25

4-Phenylbenz(2-naphthylidene)hydrazide (Compound 125)

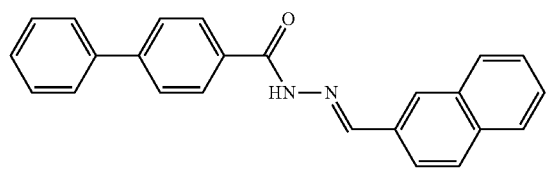 [SMILES: O=C(N/N=C/c1ccc2ccccc2c1)c1ccc(-c2ccccc2)cc1]

Compound 125 above was prepared according to the procedure described in Scheme VI above from 2-naphthaldehyde and 4-phenylbenzoic acid. The molecular weight of $C_{24}H_{18}N_2O$ is 350.41; m/z 351.15 (MH$^+$).

Example 26

4-Hydroxybenz(2-naphthylidene)hydrazide (Compound 126)

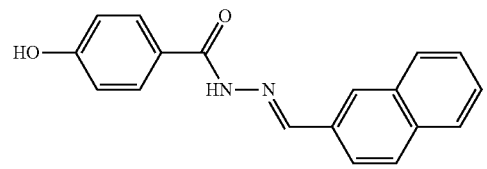

Compound 126 above was prepared according to the procedure described in Scheme VI above from 2-naphthaldehyde and 4-hydroxybenzoic acid. The molecular weight of $C_{18}H_{14}N_2O_2$ is 290.32; m/z 291.11 (MH$^+$).

Example 27

4-(2-Oxopyrrolidino-1-)benz(4-dimethylaminobenzylidene)hydrazide (Compound 127)

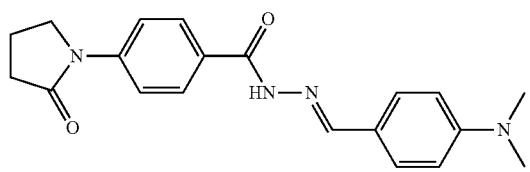 [SMILES: CN(C)c1ccc(/C=N/NC(=O)c2ccc(N3CCCC3=O)cc2)cc1]

Compound 127 above was prepared according to the procedure described in Scheme VI above from 4-dimethylaminobenzaldehyde and 4-(2-oxopyrrolidino-1-)benzoic acid. The molecular weight of $C_{20}H_{22}N_4O_2$ is 350.41; m/z 351.18 (MH$^+$).

Example 28

4-Methoxybenz(3-methoxybenzylidene)hydrazide (Compound 128)

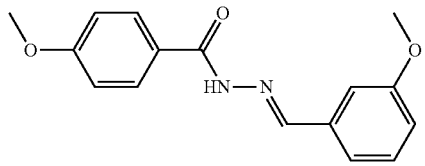 [SMILES: COc1ccc(C(=O)N/N=C/c2cccc(OC)c2)cc1]

Compound 128 above was prepared according to the procedure described in Scheme VI above from 3-methoxybenzaldehyde and 4-methoxybenzoic acid. The molecular weight of $C_{16}H_{16}N_2O_3$ is 284.31; m/z 285.12 (MH$^+$).

Example 29

4-(2-Oxopyrrolidino-1-)benz(2-hydroxy-5-methoxybenzylidene)hydrazide (Compound 129)

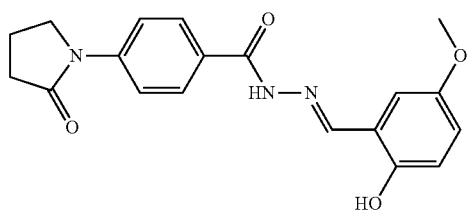 [SMILES: COc1ccc(O)c(/C=N/NC(=O)c2ccc(N3CCCC3=O)cc2)c1]

Compound 129 above was prepared according to the procedure described in Scheme VI above from 2-hydroxy-5-methoxybenzaldehyde and 4-(2-oxopyrrolidino-1-)benzoic acid. The molecular weight of $C_{19}H_{19}N_3O_4$ is 353.37; m/z 354.14 (MH$^+$).

Example 30

4-(2-Oxopyrrolidino-1-)benz(4-hydroxy-3-methoxybenzylidene)hydrazide (Compound 130)

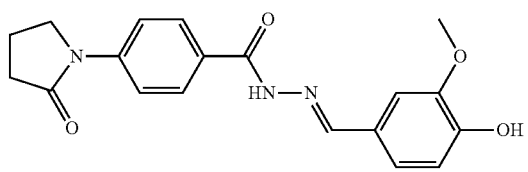 [SMILES: COc1cc(/C=N/NC(=O)c2ccc(N3CCCC3=O)cc2)ccc1O]

Compound 130 above was prepared according to the procedure described in Scheme VI above from 4-hydroxy-3-methoxybenzaldehyde and 4-(2-oxopyrrolidino-1-)benzoic acid. The molecular weight of $C_{19}H_{19}N_3O_4$ is 353.37; m/z 354.14 (MH$^+$).

Example 31

4-(2-Oxopyrrolidino-1-)benz(4-methoxybenzylidene)hydrazide (Compound 131)

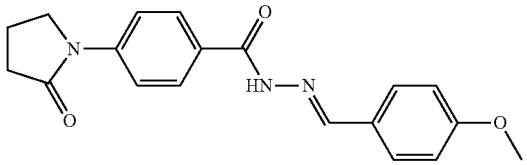

Compound 131 above was prepared according to the procedure described in Scheme VI above from 4-methoxybenzaldehyde and 4-(2-oxopyrrolidino-1-)benzoic acid. The molecular weight of $C_{19}H_{19}N_3O_3$ is 337.37; m/z 33815 (MH$^+$).

Example 32

4-(2-Oxopyrrolidino-1-)benz(3,4-dimethoxybenzylidene)hydrazide (Compound 132)

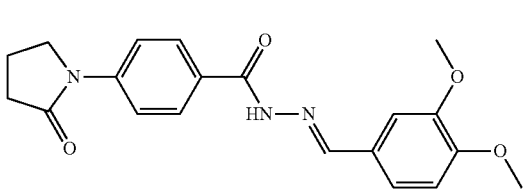 [SMILES: COc1ccc(/C=N/NC(=O)c2ccc(N3CCCC3=O)cc2)cc1OC]

Compound 132 above was prepared according to the procedure described in Scheme VI above from 3,4-dimethoxybenzaldehyde and 4-(2-oxopyrrolidino-1-)benzoic acid. The molecular weight of $C_{20}H_{21}N_3O_4$ is 367.15; m/z 368.16 (MH$^+$).

Example 33

4-(4-Chlorobenzyloxy)benz(3-methoxybenzylidene)hydrazide (Compound 133)

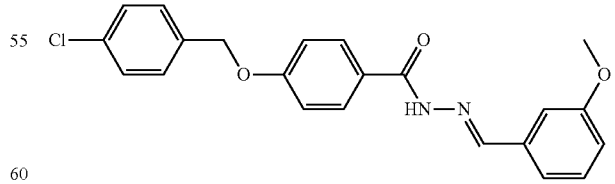

Compound 133 above was prepared according to the procedure described in Scheme VI above from 3-methoxybenzaldehyde and 4-(4-chlorobenzyloxy)benzoic acid. The molecular weight of $C_{22}H_{19}ClN_2O_3$ is 394.11; m/z 396.11 (MH$^+$).

Example 34

4-(4-Methylbenzyloxy)benz(3-methoxybenzylidene)hydrazide (Compound 134)

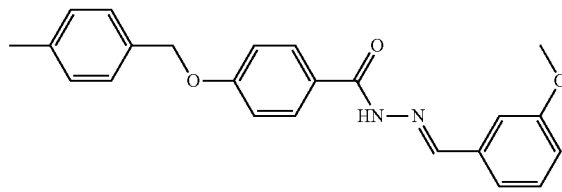

Compound 134 above was prepared according to the procedure described in Scheme VI above from 3-methoxybenzaldehyde and 4-(4-methylbenzyloxy)benzoic acid. The molecular weight of $C_{23}H_{22}N_2O_3$ is 374.16; m/z 375.17 (MH$^+$).

Example 35

4-(1-Pyrrolyl)benz(3-methoxybenzylidene)hydrazide (Compound 135)

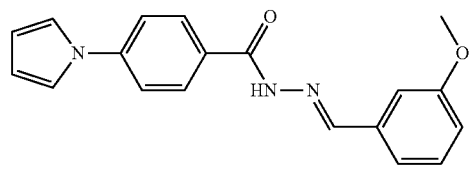 [SMILES: COc1cccc(/C=N/NC(=O)c2ccc(-n3cccc3)cc2)c1]

Compound 135 above was prepared according to the procedure described in Scheme VI above from 3-methoxybenzaldehyde and 4-(1-pyrrolyl)benzoic acid. The molecular weight of $C_{19}H_{17}N_3O_2$ is 319.36; m/z 320.14 (MH$^+$).

Example 36

4-(4-Methylbenzyloxy)benz(3,4,5-trimethoxybenzylidene)hydrazide (Compound 136)

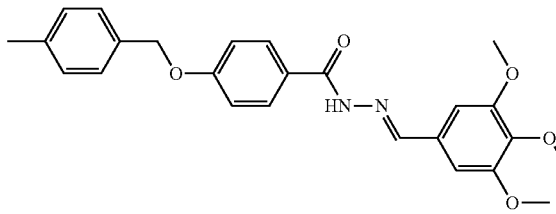

Compound 136 above was prepared according to the procedure described in Scheme VI above from 3,4,5-trimethoxybenzaldehyde and 4-(4-methylbenzyloxy)benzoic acid. The molecular weight of $C_{25}H_{26}N_2O_5$ is 434.48; m/z 435.19 (MH$^+$).

Example 37

4-(4-Chlorobenzyloxy)benz(3,4-dimethoxybenzylidene)hydrazide (Compound 137)

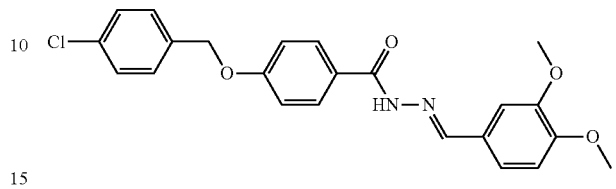

Compound 137 above was prepared according to the procedure described in Scheme VI above from 3,4-dimethoxybenzaldehyde and 4-(4-chlorobenzyloxy)benzoic acid. The molecular weight of $C_{23}H_{21}ClN_2O_4$ is 424.88; m/z 426.12 (MH$^+$).

Example 38

4-(4-Methylbenzyloxy)benz(3,4-dimethoxybenzylidene)hydrazide (Compound 138)

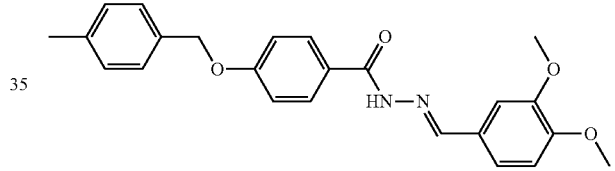

Compound 138 above was prepared according to the procedure described in Scheme VI above from 3,4-dimethoxybenzaldehyde and 4-(4-methylbenzyloxy)benzoic acid. The molecular weight of $C_{24}H_{24}N_2O_4$ is 404.46; m/z 405.18 (MH$^+$).

Example 39

4-Dimethylaminobenz(3-methoxybenzylidene)hydrazide (Compound 139)

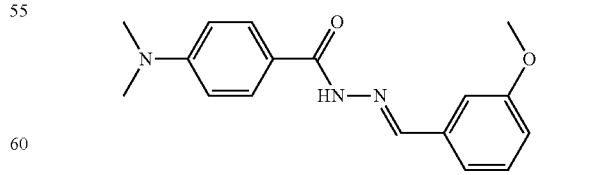

Compound 139 above was prepared according to the procedure described in Scheme VI above from 3-methoxybenzaldehyde and 4-dimethylaminobenzoic acid. The molecular weight of $C_{17}H_{19}N_3O_2$ is 297.35; m/z 298.15 (MH$^+$).

Example 40

4-Phenylbenz(3-methoxybenzylidene)hydrazide (Compound 140)

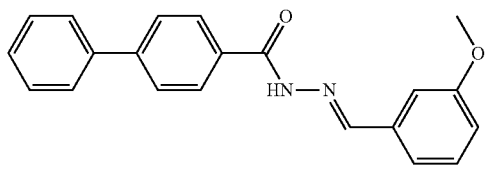

Compound 140 above was prepared according to the procedure described in Scheme VI above from 3-methoxybenzaldehyde and 4-phenylbenzoic acid. The molecular weight of $C_{21}H_{18}N_2O_2$ is 330.38; m/z 331.14 (MH$^+$).

Example 41

4-(4-Chlorobenzyloxy)benz(4-hydroxy-3-methoxybenzylidene)hydrazide (Compound 141)

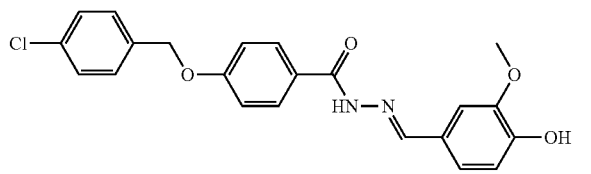 [SMILES: COc1cc(/C=N/NC(=O)c2ccc(OCc3ccc(Cl)cc3)cc2)ccc1O]

Compound 141 above was prepared according to the procedure described in Scheme VI above from 4-hydroxy-3-methoxybenzaldehyde and 4-(4-chlorobenzyloxy)benzoic acid. The molecular weight of $C_{22}H_{19}ClN_2O_4$ is 410.85; m/z 412.10 (MH$^+$).

Example 42

4-(4-Bromobenzyloxy)benz(3-methoxybenzylidene)hydrazide (Compound 142)

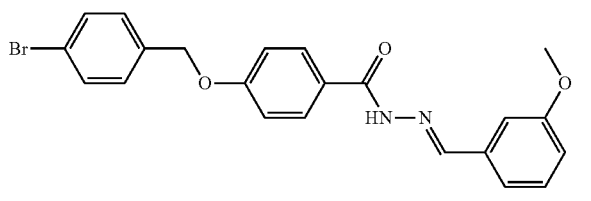 [SMILES: COc1cccc(/C=N/NC(=O)c2ccc(OCc3ccc(Br)cc3)cc2)c1]

Compound 142 above was prepared according to the procedure described in Scheme VI above from 3-methoxybenzaldehyde and 4-(4-bromobenzyloxy)benzoic acid. The molecular weight of $C_{22}H_{19}BrN_2O_3$ is 439.30; m/z 438.06 (MH$^+$).

Example 43

4-(4-Fluorobenzyloxy)benz(3-methoxybenzylidene)hydrazide (Compound 143)

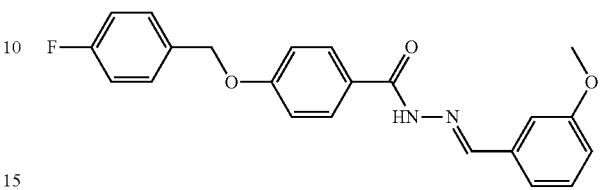

Compound 143 above was prepared according to the procedure described in Scheme VI above from 3-methoxybenzaldehyde and 4-(4-fluorobenzyloxy)benzoic acid. The molecular weight of $C_{22}H_{19}FN_2O_3$ is 378.40; m/z 379.14 (MH$^+$).

Example 44

4-Phenylbenz(4-hydroxy-3-methoxybenzylidene)hydrazide (Compound 144)

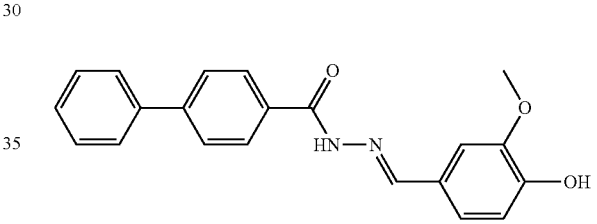

Compound 144 above was prepared according to the procedure described in Scheme VI above from 4-hydroxy-3-methoxybenzaldehyde and 4-phenylbenzoic acid. The molecular weight of $C_{21}H_{18}N_2O_3$ is 346.38; m/z 347.14 (MH$^+$).

Example 45

4-Diethylaminobenz(3-methoxybenzylidene)hydrazide (Compound 145)

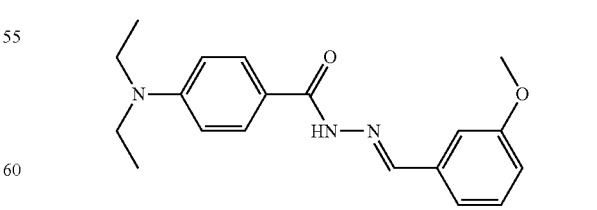

Compound 145 above was prepared according to the procedure described in Scheme VI above from 3-methoxybenzaldehyde and 4-diethylaminobenzoic acid. The molecular weight of $C_{19}H_{23}N_3O_2$ is 325.40; m/z 326.18 (MH$^+$).

Example 46

3-(2-Naphthylpyrazolyl-5-)carboxyl(3-methoxybenzylidene)hydrazide (Compound 146)

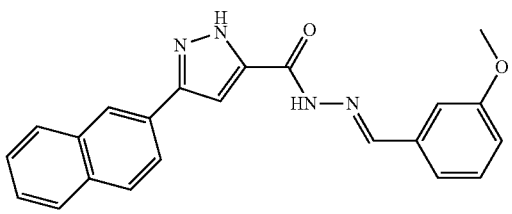 [SMILES: COc1cccc(/C=N/NC(=O)c2cc(-c3ccc4ccccc4c3)n[nH]2)c1]

Compound 146 above was prepared according to the procedure described in Scheme VI above from 3-methoxybenzaldehyde and 3-(2-Naphthylpyrazolyl-5-)carboxylic acid. The molecular weight of $C_{22}H_{18}N_4O_2$ is 370.40; m/z 371.15 (MH$^+$).

Example 47

3-(4-(2-Methylpropyl)phenylpyrazolyl-5-)carboxyl (3-methoxybenzylidene)hydrazide (Compound 147)

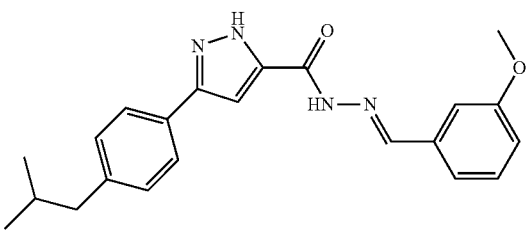 [SMILES: COc1cccc(/C=N/NC(=O)c2cc(-c3ccc(CC(C)C)cc3)n[nH]2)c1]

Compound 147 above was prepared according to the procedure described in Scheme VI above from 3-methoxybenzaldehyde and 3-(4-(2-methylpropyl)phenylpyrazolyl-5-)carboxylic acid. The molecular weight of $C_{22}H_{24}N_4O_2$ is 376.45; m/z 377.19 (MH$^+$).

Example 48

Octadecano(2-hydroxy-5-methoxybenzylidene)hydrazide (Compound 148)

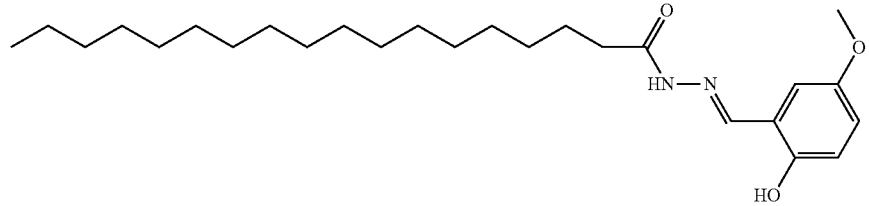 [SMILES: CCCCCCCCCCCCCCCCCC(=O)N/N=C/c1cc(OC)ccc1O]

Compound 148 above was prepared according to the procedure described in Scheme VI above from 2-hydroxy-5-methoxybenzaldehyde and octadecanolic acid. The molecular weight of $C_{26}H_{44}N_2O_3$ is 432.64; m/z? (MH$^+$).

Example 49

4-Benzyloxybenz(3-methoxybenzylidene)hydrazide (Compound 149)

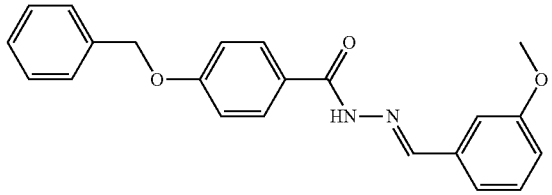 [SMILES: COc1cccc(/C=N/NC(=O)c2ccc(OCc3ccccc3)cc2)c1]

Compound 149 above was prepared according to the procedure described in Scheme VI above from 3-methoxybenzaldehyde and 4-benzyloxybenzoic acid. The molecular weight of $C_{22}H_{20}N_2O_3$ is 360.41; m/z 361.15 (MH$^+$).

Example 50

4-(4-Oxazolyl)benz(3-methoxybenzylidene)hydrazide (Compound 150)

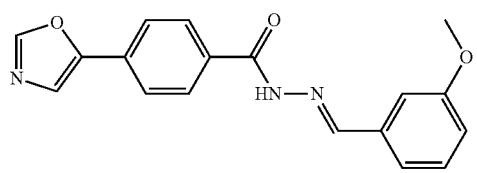 [SMILES: COc1cccc(/C=N/NC(=O)c2ccc(-c3cnco3)cc2)c1]

Compound 150 above was prepared according to the procedure described in Scheme VI above from 3-methoxybenzaldehyde and 4-(4-oxazolyl)benzoic acid. $^1$H NMR (500 MHz, DMSO) 8.53 (s, 1H), 8.44 (s, 1H), 8.01 (d, 2H), 7.88 (m, 3H), 7.38 (m, 1H), 7.28 (m, 2H), 7.02 (m, 1H), 3.81 (s, 3H).

Example 51

4-Phenylbenz(2-hydroxy-5-methoxybenzylidene)hydrazide (Compound 151)

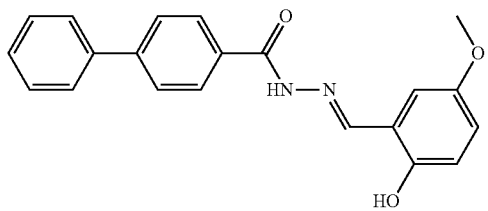 [SMILES: COc1ccc(O)c(/C=N/NC(=O)c2ccc(-c3ccccc3)cc2)c1]

Compound 151 above was prepared according to the procedure described in Scheme VI above from 2-hydroxy-5-methoxybenzaldehyde and 4-phenylbenzoic acid. $^1$H NMR (500 MHz, DMSO) 8.64 (s, 1H), 8.02 (d, 2H), 7.84 (d, 2H), 7.76 (d, 2H), 7.50 (m, 2H), 7.42 (m, 1H), 7.13 (d, 1H), 6.84-6.92 (m, 2H), 3.73 (s, 3H).

Example 52

4-(4-Methoxybenzyloxy)benz(3-methoxybenzylidene)hydrazide (Compound 152)

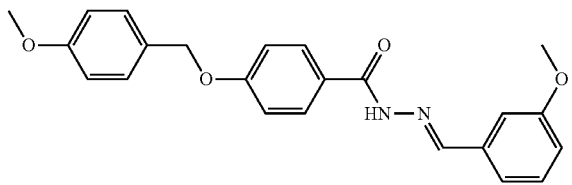 [SMILES: COc1ccc(COc2ccc(C(=O)N/N=C/c3cccc(OC)c3)cc2)cc1]

Compound 152 above was prepared according to the procedure described in Scheme VI above from 3-methoxybenzaldehyde and 4-(4-methoxybenzyloxy)benzoic acid. The molecular weight of $C_{23}H_{22}N_2O_4$ is 390.43; m/z (MH$^+$): calculated 391.16 and observed 391.10.

Example 53

4-(3-Chlorobenzyloxy)benz(3-methoxybenzylidene)hydrazide (Compound 153)

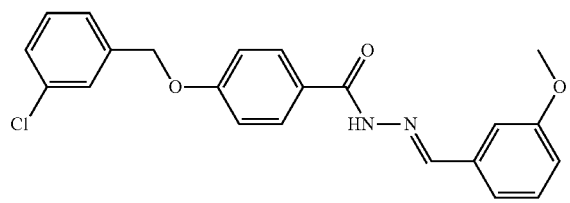 [SMILES: COc1cccc(/C=N/NC(=O)c2ccc(OCc3cccc(Cl)c3)cc2)c1]

Compound 153 above was prepared according to the procedure described in Scheme VI above from 3-methoxybenzaldehyde and 4-(3-chlorobenzyloxy)benzoic acid. $^1$H NMR (500 MHz, CD3OD) 8.28 (s, 1H), 7.93 (m, 2H), 7.56 (br, 1H), 7.49 (m, 1H), 7.26-7.40 (m, 5H), 7.13 (m, 2H), 6.98 (m, 1H), 5.19 (s, 2H), 3.86 (s, 3H).

Example 54

4-(4-Trifluoromethylbenzyloxy)benz(3-methoxybenzylidene)hydrazide (Compound 154)

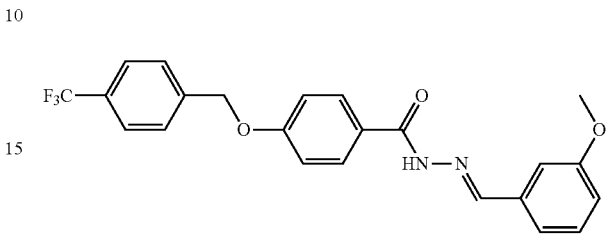

Compound 154 above was prepared according to the procedure described in Scheme VI above from 3-methoxybenzaldehyde and 4-(4-Trifluoromethylbenzyloxy)benzoic acid. $^1$H NMR (500 MHz, CD$_3$COCD$_3$) 8.46 (br, 1H), 8.00 (d, 2H), 7.76 (m, 4H), 7.24-7.36 (m, 3H), 7.15 (d, 2H), 6.98 (m, 1H), 5.35 (s, 2H), 3.83 (s, 3H).

Example 55

4-(3-Methoxybenzyloxy)benz(3-methoxybenzylidene)hydrazide (Compound 155)

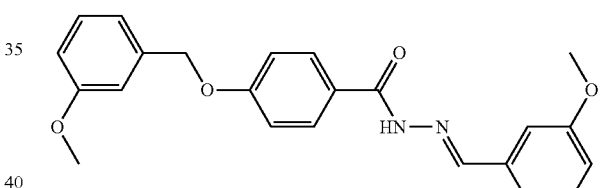

Compound 155 above was prepared according to the procedure described in Scheme VI above from 3-methoxybenzaldehyde and 4-(3-methoxybenzyloxy)benzoic acid. $^1$H NMR (500 MHz, CD$_3$COCD$_3$) 8.54 (br, 1H), 8.04 (m, 2H), 7.22-7.34 (m, 4H), 7.09 (d, 2H), 7.04 (m, 2H), 6.88-6.94 (m, 2H), 5.14 (s, 2H), 3.79 (s, 3H), 3.76 (s, 3H).

Example 56

4-(4-Vinylbenzyloxy)benz(3-methoxybenzylidene)hydrazide (Compound 156)

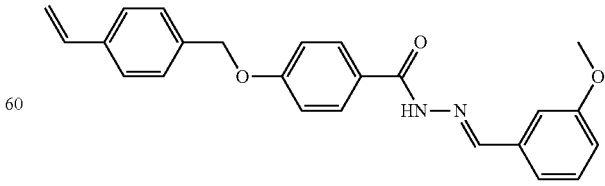

Compound 156 above was prepared according to the procedure described in Scheme VI above from 3-methoxybenzaldehyde and 4-(4-vinylbenzyloxy)benzoic acid. The molecular weight of $C_{24}H_{22}N_2O_3$ is 386.44; m/z (MO: calculated 387.17 and observed 387.00.

Example 57

4-(2-Naphthylmethoxy)benz(3-methoxybenzylidene)hydrazide (Compound 157)

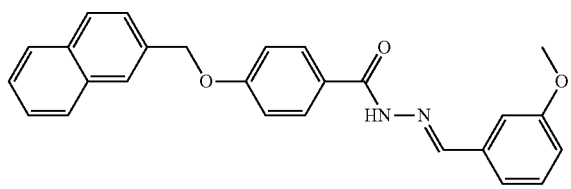 [SMILES: COc1cccc(/C=N/NC(=O)c2ccc(OCc3ccc4ccccc4c3)cc2)c1]

Compound 157 above was prepared according to the procedure described in Scheme VI above from 3-methoxybenzaldehyde and 4-(2-naphthylmethoxy)benzoic acid. The molecular weight of $C_{26}H_{22}N_2O_3$ is 410.46; m/z ($MH^+$): calculated 411.17 and observed 411.00.

Example 58

4-((2-Phenylthiazolyl-4-)methoxy)benz(3-methoxybenzylidene)hydrazide (Compound 158)

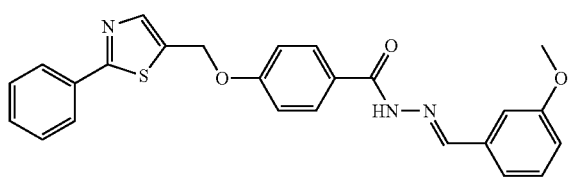 [SMILES: COc1cccc(/C=N/NC(=O)c2ccc(OCc3cnc(-c4ccccc4)s3)cc2)c1]

Compound 158 above was prepared according to the procedure described in Scheme VI above from 3-methoxybenzaldehyde and 4-((2-phenylthiazolyl-4-)methoxy)benzoic acid. $^1$H NMR (500 MHz, $CD_3COCD_3$) 8.46 (br, 1H), 8.01 (d, 2H), 7.99 (m, 2H), 7.50 (m, 3H), 7.34 (t, 2H), 7.27 (m, 1H), 7.17 (d, 2H), 6.98 (m, 1H), 5.45 (s, 2H), 3.84 (s, 3H), 2.51 (s, 3H).

Example 59

4-Phenylbenz(4-fluoro-3-methoxybenzylidene)hydrazide (Compound 159)

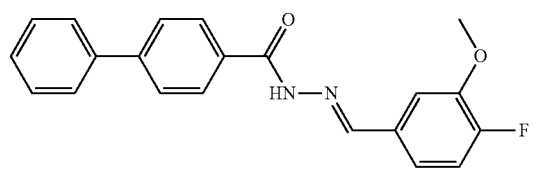 [SMILES: COc1cc(/C=N/NC(=O)c2ccc(-c3ccccc3)cc2)ccc1F]

Compound 159 above was prepared according to the procedure described in Scheme VI above from 4-fluoro-3-methoxybenzaldehyde and 4-phenylbenzoic acid. The molecular weight of $C_{21}H_{17}FN_2O_2$ is 348.37; m/z ($MH^+$): calculated 349.13 and observed 349.14.

Example 60

4-Phenylbenz(3,5-dimethoxybenzylidene)hydrazide (Compound 160)

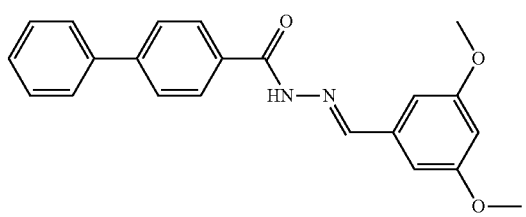 [SMILES: COc1cc(/C=N/NC(=O)c2ccc(-c3ccccc3)cc2)cc(OC)c1]

Compound 160 above was prepared according to the procedure described in Scheme VI above from 3,5-dimethoxybenzaldehyde and 4-phenylbenzoic acid. The molecular weight of $C_{22}H_{20}N_2O_3$ is 360.41; m/z ($MH^+$): calculated 361.15 and observed 361.15.

Example 61

4-(2-Fluorophenyl)phenylbenz(3-methoxybenzylidene)hydrazide (Compound 161)

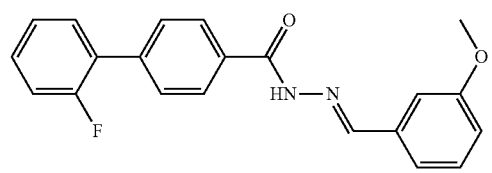

Compound 161 above was prepared according to the procedure described in Scheme VI above from 3-methoxybenzaldehyde and 4-(2-fluorophenyl)benzoic acid. The molecular weight of $C_{21}H_{17}FN_2O_2$ is 348.37; m/z ($MH^+$): calculated 349.13 and observed 349.10.

Example 62

4-Methylaminobenz(3-methoxybenzylidene)hydrazide (Compound 162)

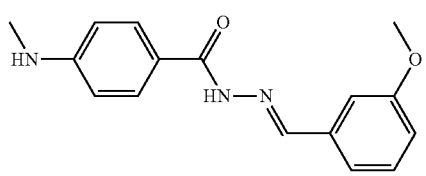 [SMILES: CNc1ccc(C(=O)N/N=C/c2cccc(OC)c2)cc1]

Compound 162 above was prepared according to the procedure described in Scheme VI above from 3-methoxybenzaldehyde and 4-methylaminobenzoic acid. The molecular weight of $C_{16}H_{17}N_3O_2$ is 283.33; m/z (MH⁺): calculated 284.14 and observed 284.10.

Example 63

4-Phenylbenz(5-indolidene)hydrazide (Compound 163)

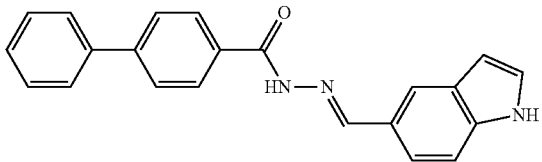 [SMILES: O=C(N/N=C/c1ccc2[nH]ccc2c1)c1ccc(-c2ccccc2)cc1]

Compound 163 above was prepared according to the procedure described in Scheme VI above from 4-phenylbenzoic acid and 5-indolecarboxaldehyde. The molecular weight of $C_{22}H_{17}N_3O$ is 339.39; m/z 340.14 (MH⁺).

Example 64

4-Phenylbenz(3-vinylbenzylidene)hydrazide (Compound 164)

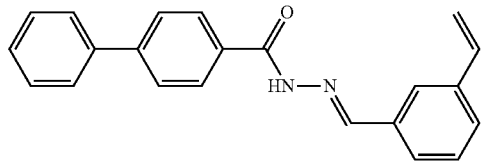 [SMILES: C=Cc1cccc(/C=N/NC(=O)c2ccc(-c3ccccc3)cc2)c1]

Compound 164 above was prepared according to the procedure described in Scheme VI above from 3-vinylbenzaldehyde and 4-phenylbenzoic acid. ¹H NMR (DMSO, 500 MHz) 11.94 (s), 8.49 (s), 8.02 (d), 5.90 (d), and 5.35 (d).

Example 65

4-Phenylbenz(3-acetylbenzylidene)hydrazide (Compound 165)

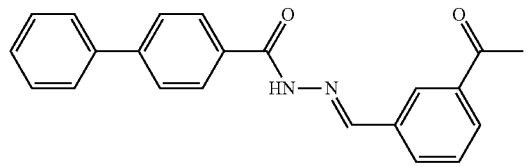 [SMILES: CC(=O)c1cccc(/C=N/NC(=O)c2ccc(-c3ccccc3)cc2)c1]

Compound 165 above was prepared according to the procedure described in Scheme VI above from 3-acetylbenzaldehyde and 4-phenylbenzoic acid. ¹H NMR (CDCl₃, 500 MHz) 10.49 (s), 8.57 (s), 8.13 (s), and 2.54 (s).

Example 66

4-Dimethylaminobenz(3-acetylbenzylidene)hydrazide (Compound 166)

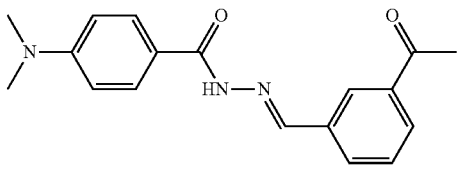 [SMILES: CC(=O)c1cccc(/C=N/NC(=O)c2ccc(N(C)C)cc2)c1]

Compound 166 above was prepared according to the procedure described in Scheme VI above from 3-acetylbenzaldehyde and 4-dimethylaminobenzoic acid. NMR (DMSO, 500 MHz) 11.63 (s), 8.49 (s), 8.23 (s), 7.99 (d), 7.94 (d), 7.82 (d), 7.60 (t), and 6.75 (d).

Example 67

4-Dimethylaminobenz(3-vinylbenzylidene)hydrazide (Compound 167)

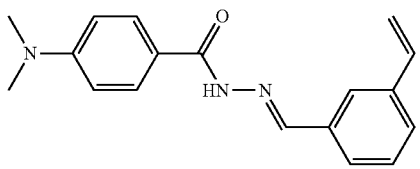 [SMILES: C=Cc1cccc(/C=N/NC(=O)c2ccc(N(C)C)cc2)c1]

Compound 167 above was prepared according to the procedure described in Scheme VI above from 3-vinylbenzaldehyde and 4-dimethylaminobenzoic acid. ¹H NMR (DMSO, 500 MHz) 11.58 (s), 8.42 (s), 7.82 (d), 7.25 (s), 7.60 (d), 7.53 (d), 7.42 (t), and 2.99 (s).

Example 68

4-Dimethylaminobenz(3-methoxybenzylidene)hydrazide (Compound 168)

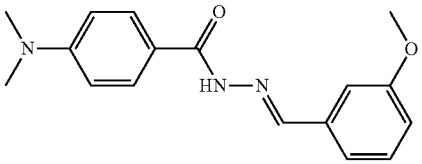

Compound 168 above was prepared according to the procedure described in Scheme VI above from 3-methoxybenzaldehyde and 4-dimethylaminobenzoic acid. ¹H NMR (500 MHz, CDCl₃) 7.29 (d, J 8.0, 1H), 7.24 (d, J 8.0, 1H), 7.08-7.05 (m, 3H), 7.01 (d, J 7.5, 1H), 6.88 (ddd, J 7.5, 6.5 and 1.5, 1H), 6.77 (dd, J 8.5 and 2.5, 1H), 6.33 (s, 1H), 3.81 (s, 3H), 2.98 (s, 6H).

Example 69

4-Dimethylaminobenz(3-phenylacetyleneben-zylidene)hydrazide (Compound 169)

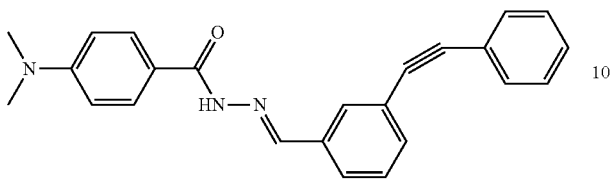

Compound 169 above was prepared according to the procedure described in Scheme VI above from 3-phenylacetyle-nebenzaldehyde and 4-dimethylaminobenzoic acid. $^1$H NMR (500 MHz, DMSO) 11.64 (s, 1H), 8.42 (s, 1H), 7.88 (s, 1H), 7.82 (d, J 7.5, 2H), 7.73 (d, J 8.0, 1H), 7.61-7.57 (m, 3H), 7.51 (t, J 7.5, 1H), 7.45-7.43 (m, 3H), 6.76 (d, J 9.0, 2H), and 3.00 (s, 6H).

Example 70

4-Dimethylaminobenz(3-(2E-phenylethenyl)ben-zylidene)hydrazide (Compound 170)

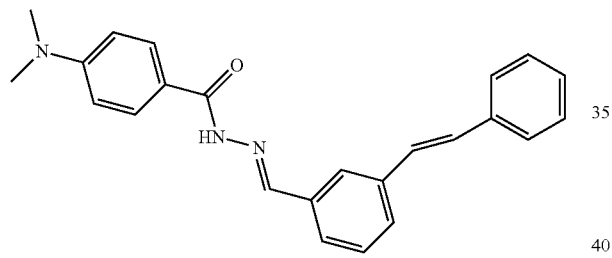

Compound 170 above was prepared according to the procedure described in Scheme VI above from 3-(2E-phe-nylethenyl)benzaldehyde and 4-dimethylaminobenzoic acid. $^1$H NMR (500 MHz, DMSO) 11.58 (s, 1H), 8.45 (s, 1H), 7.83 (d, J 8.5, 2H), 7.68-7.64 (m, 2H), 7.60 (d, J 7.5, 2H), 7.46 (t, J 7.5, 1H), 7.39 (t, J 8.0, 2H), 7.33 (d, J 4.0, 2H), 7.29 (t, J 7.5, 1H) 6.76 (d, J 9.0, 2H), and 3.00 (s, 6H).

Example 71

4-Dimethylaminobenz(3-hydroxymethylben-zylidene)hydrazide (Compound 171)

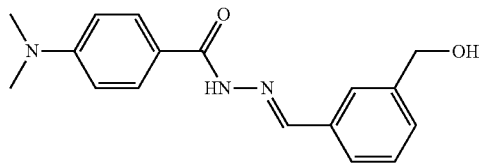 [SMILES: CN(C)c1ccc(C(=O)N/N=C/c2cccc(CO)c2)cc1]

Compound 171 above was prepared according to the procedure described in Scheme VI above from 3-hydroxymeth-ylbenzaldehyde and 4-dimethylaminobenzoic acid. $^1$H NMR (500 MHz, DMSO) 11.52 (s, 1H), 8.41 (s, 1H), 7.82 (d, J 9.0, 2H), 7.69 (s, 1H), 7.53 (d, J 8.0, 1H), 7.39 (t, J 7.5, 1H), 7.34 (d, J 7.5, 1H), 6.75 (d, J 9.0, 2H), 4.55 (d, J 5.5, 2H), and 2.99 (s, 6H).

Example 72

5-Methoxyindole-2-carboxyl(2-hydroxy-5-methoxy-benzylidene)hydrazide (Compound 172)

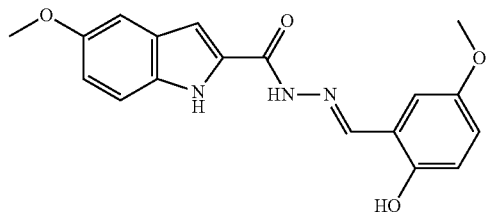 [SMILES: COc1ccc(O)c(/C=N/NC(=O)c2cc3cc(OC)ccc3[nH]2)c1]

Compound 172 above was prepared according to the procedure described in Scheme VI above from 2-hydroxy-5-methoxybenzaldehyde and 5-methoxyindole-2-carboxylic acid. The molecular weight of $C_{18}H_{17}N_3O_4$ is 339.35; m/z (M$^+$): calculated 340.12 and observed 340.06.

Example 73

5-Indolyloxoacet(2-hydroxy-5-methoxybenzylidene)hydrazide (Compound 173)

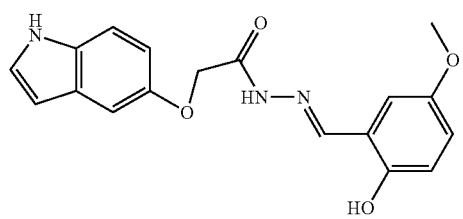 [SMILES: COc1ccc(O)c(/C=N/NC(=O)COc2ccc3[nH]ccc3c2)c1]

Compound 173 above was prepared according to the procedure described in Scheme VI above from 2-hydroxy-5-methoxybenzaldehyde and 5-indolyloxoacetic acid. The molecular weight of $C_{18}H_{17}N_3O_4$ is 339.35; m/z (MH$^+$): calculated 340.13 and observed 399.99.

Example 74

5-Hydroxybenzofuran-2-carboxyl(2-hydroxy-5-methoxybenzylidene)hydrazide (Compound 174)

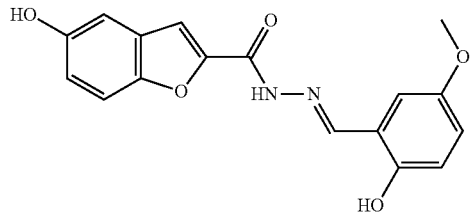 [SMILES: COc1ccc(O)c(/C=N/NC(=O)c2cc3cc(O)ccc3o2)c1]

Compound 174 above was prepared according to the procedure described in Scheme VI above from 2-hydroxy-5-methoxybenzaldehyde and 5-hydroxybenzofuran-2-carboxylic acid. The molecular weight of $C_{17}H_{14}N_2O_5$ is 326.30; m/z (MH$^+$): calculated 327.09 and observed 326.98.

Example 75

5-Hydroxyindole-2-carboxyl(2-hydroxy-5-methoxybenzylidene)hydrazide (Compound 175)

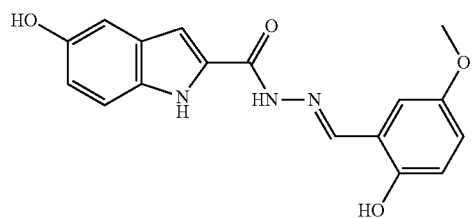 [SMILES: COc1ccc(O)c(/C=N/NC(=O)c2cc3cc(O)ccc3[nH]2)c1]

Compound 175 above was prepared according to the procedure described in Scheme VI above from 2-hydroxy-5-methoxybenzaldehyde and 5-hydroxyindole-2-carboxylic acid. The molecular weight of $C_{17}H_{15}N_3O_4$ is 325.32; m/z (MH$^+$): calculated 326.11 and observed 325.90.

Example 76

5-Hydroxybenzofuran-2-carboxyl(3-methoxymethylbenzylidene)hydrazide (Compound 176)

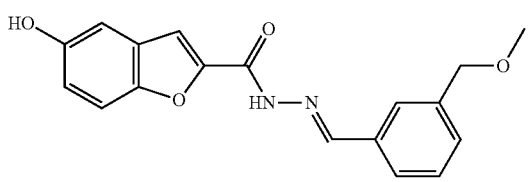 [SMILES: COCc1cccc(/C=N/NC(=O)c2cc3cc(O)ccc3o2)c1]

Compound 176 above was prepared according to the procedure described in Scheme VI above from 3-methoxymethylbenzaldehyde and 5-hydroxybenzofuran-2-carboxylic acid. The molecular weight of $C_{18}H_{16}N_2O_4$ is 324.33; m/z (MH$^+$): calculated 325.11 and observed 324.96.

Example 77

4-Dimethylaminobenz(3-dimethylaminobenzylidene)hydrazide (Compound 177)

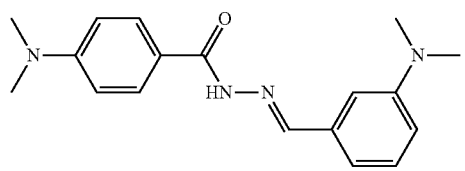

Compound 177 above was prepared according to the procedure described in Scheme VI above from 3-dimethylaminobenzaldehyde and 4-dimethylaminobenzoic acid. $^1$H NMR (DMSO, 500 MHz) 11.43 (s), 8.36 (s), 7.80 (d), 7.24 (t), 7.01 (s), 6.74 (d), 2.99 (s), and 2.96 (s).

Example 78

4-Dimethylaminobenz(3-bromo-5-indolidene)hydrazide (Compound 178)

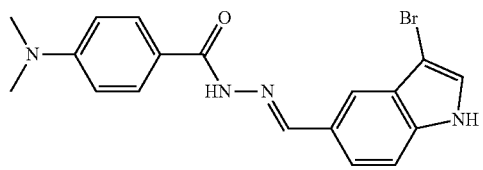 [SMILES: CN(C)c1ccc(C(=O)N/N=C/c2ccc3[nH]cc(Br)c3c2)cc1]

Compound 178 above was prepared according to the procedure described in Scheme VI above from 4-dimethylaminobenzoic acid and 3-bromo-5-indolecarboxaldehyde. $^1$H NMR (DMSO, 500 MHz) 11.68 (s), 11.43 (s), 8.50 (s), 7.82 (d), 7.68 (s), 7.48 (d), 6.75 (d), and 2.99 (s).

Example 79

4-Dimethylaminobenz(2E-ethylaminocarboxyethenylbenzylidene)hydrazide (Compound 179)

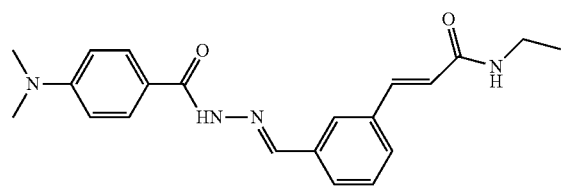 [SMILES: CCNC(=O)/C=C/c1cccc(/C=N/NC(=O)c2ccc(N(C)C)cc2)c1]

Compound 179 above was prepared according to the procedure described in Scheme VI above from 2E-ethylaminocarboxyethenylbenzaldehyde and 4-dimethylaminobenzoic acid. The molecular weight of $C_{21}H_{24}N_4O_2$ is 364.44; m/z (MH$^+$): calculated 365.19 and observed 365.06.

Example 80

4-Dimethylaminobenz(3-chloro-6-indolidene)hydrazide (Compound 180)

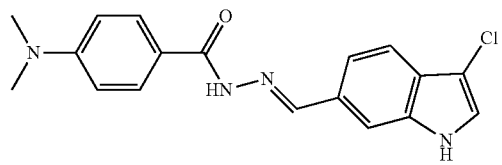 [SMILES: CN(C)c1ccc(C(=O)N/N=C/c2ccc3c(Cl)c[nH]c3c2)cc1]

Compound 180 above was prepared according to the procedure described in Scheme VI above from 4-dimethylaminobenzoic acid and 3-chloro-6-indolecarboxaldehyde. $^1$H NMR (DMSO, 500 MHz) 11.58 (s), 11.43 (s), 8.48 (s), 7.81 (d), 7.74 (s), 7.62 (d), 7.46 (d), 6.74 (d), and 2.99 (s).

Example 81

4-Dimethylaminobenz(2E-(2-methylphenyl)ethenyl-benzylidene)hydrazide (Compound 181)

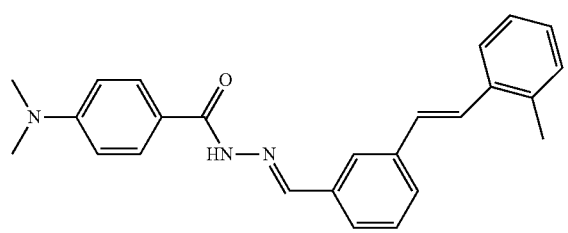 [SMILES: Cc1ccccc1/C=C/c1cccc(/C=N/NC(=O)c2ccc(N(C)C)cc2)c1]

Compound 181 above was prepared according to the procedure described in Scheme VI above from 2E-(2-methylphenyl)ethenylbenzaldehyde and 4-dimethylaminobenzoic acid. $^1$H NMR (DMSO, 500 MHz) 11.59 (s), 8.46 (s), 7.88 (s), 7.82 (d), 7.61 (d), 6.75 (d), 2.99 (s), and 2.41 (s).

Example 82

4-Dimethylaminobenz(2E-(3-chlorophenyl)ethenyl-benzylidene)hydrazide (Compound 182)

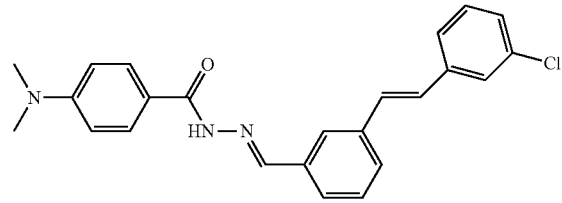 [SMILES: CN(C)c1ccc(C(=O)N/N=C/c2cccc(/C=C/c3cccc(Cl)c3)c2)cc1]

Compound 182 above was prepared according to the procedure described in Scheme VI above from 2E-(3-chlorophenyl)ethenylbenzaldehyde and 4-dimethylaminobenzoic acid. $^1$H NMR (DMSO, 500 MHz) 11.59 (s), 8.44 (s), 7.89 (s), 7.82 (d), 6.76 (d), and 2.99 (s).

Example 83

4-Dimethylaminobenz(2E-(4-hydroxybutyl)aminocarboxyethenylbenzylidene)hydrazide (Compound 183)

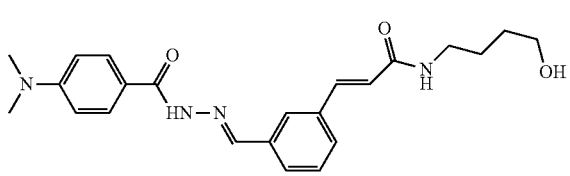 [SMILES: CN(C)c1ccc(C(=O)N/N=C/c2cccc(/C=C/C(=O)NCCCCO)c2)cc1]

Compound 183 above was prepared according to the procedure described in Scheme VI above from 2E-(4-hydroxybutyl)aminocarboxyethenylbenzaldehyde and 4-dimethylaminobenzoic acid. The molecular weight of $C_{23}H_{28}N_4O_3$ is 408.49; m/z (MH$^+$): calculated 409.22 and observed 409.04.

Example 84

4-Dimethylaminobenz(3-benzyloxymethylbenzylidene)hydrazide (Compound 184)

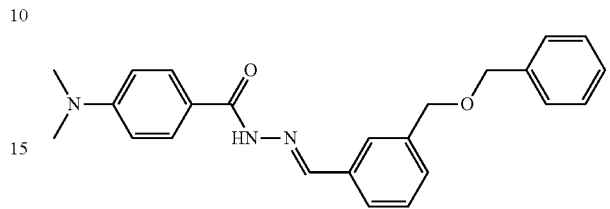

Compound 184 above was prepared according to the procedure described in Scheme VI above from 3-benzyloxymethylbenzaldehyde and 4-dimethylaminobenzoic acid. $^1$H NMR (DMSO, 500 MHz) 11.57 (s), 8.41 (s), 7.81 (d), 6.74 (d), 4.59 (s), 4.58 (s), and 2.99 (s).

Example 85

4-Dimethylaminobenz(2E-(2-chlorophenyl)ethenyl-benzylidene)hydrazide (Compound 185)

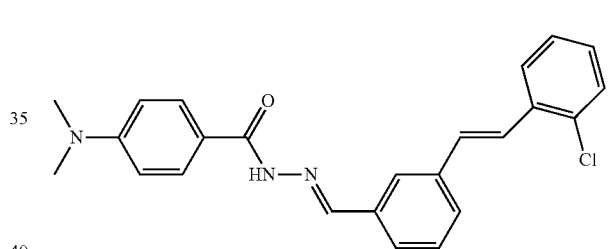

Compound 185 above was prepared according to the procedure described in Scheme VI above from 2E-(2-chlorophenyl)ethenylbenzaldehyde and 4-dimethylaminobenzoic acid. $^1$H NMR (DMSO, 500 MHz) 11.59 (s), 8.43 (s), 7.82 (d), 7.68 (d), 7.63 (d), 6.75 (d), and 2.99 (s).

Example 86

4-Dimethylaminobenz(2E-(4-chlorophenyl)ethenyl-benzylidene)hydrazide (Compound 186)

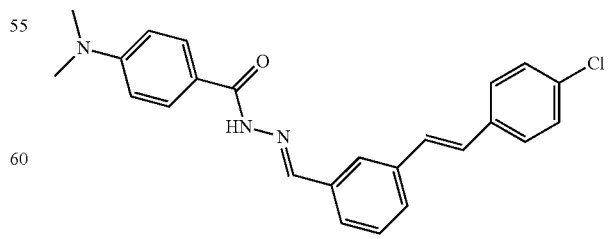

Compound 186 above was prepared according to the procedure described in Scheme VI above from 2E-(4-chlorophenyl)ethenylbenzaldehyde and 4-dimethylaminobenzoic acid.

¹H NMR (DMSO, 500 MHz) 11.59 (s), 8.44 (s), 7.89 (s), 7.67 (d), 7.60 (d), 6.76 (d), and 2.99 (s).

Example 87

4-Dimethylaminobenz(3-methoxymethylbenzylidene)hydrazide (Compound 187)

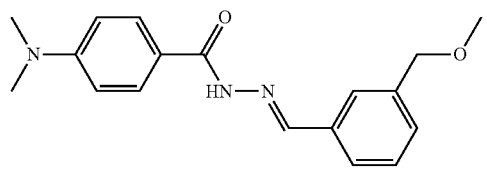

Compound 187 above was prepared according to the procedure described in Scheme VI above from 3-methoxymethylbenzaldehyde and 4-dimethylaminobenzoic acid. ¹H NMR (500 MHz, DMSO) 11.58 (s, 1H), 8.44 (s, 1H), 7.83 (d, J 9.5, 2H), 7.68 (s, 1H), 7.58 (d, J 7.5, 1H), 7.43 (t, J 7.5, 1H), 7.35 (d, J 7.5, 1H), 6.75 (d, J 7.5, 2H), 4.46 (s, 2H), 3.32 (s, 3H), and 2.99 (s, 6H).

Example 88

4-Dimethylaminobenz(3-(2-methylbenzyloxy)methylbenzylidene)hydrazide (Compound 188)

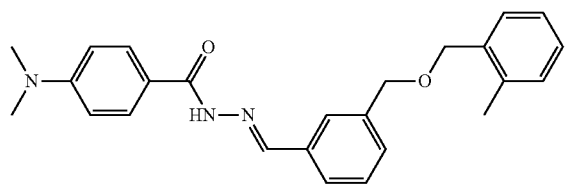 [SMILES: CN(C)c1ccc(C(=O)N/N=C/c2cccc(COCc3ccccc3)c2)cc1]

Compound 188 above was prepared according to the procedure described in Scheme VI above from 3-(2-methylbenzyloxy)methylbenzaldehyde and 4-dimethylaminobenzoic acid. ¹H NMR (CDCl₃, 500 MHz) 7.68 (d), 4.59 (s), 4.58 (s), 3.02 (s), and 2.32 (s).

Example 89

4-Dimethylaminobenz(3-(4-methylbenzyloxy)methylbenzylidene)hydrazide (Compound 189)

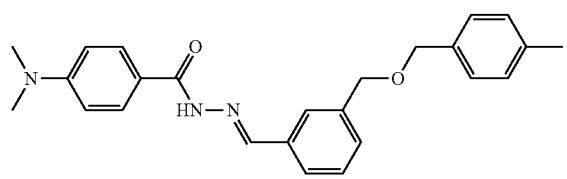

Compound 189 above was prepared according to the procedure described in Scheme VI above from 3-(4-methylbenzyloxy)methylbenzaldehyde and 4-dimethylaminobenzoic acid. ¹H NMR (CDCl₃, 500 MHz) 6.70 (d), 4.57 (s), 4.56 (s), 3.04 (s), and 2.34 (s).

Example 90

4-Dimethylaminobenz(3-benzyloxyiminomethylbenzylidene)hydrazide (Compound 190)

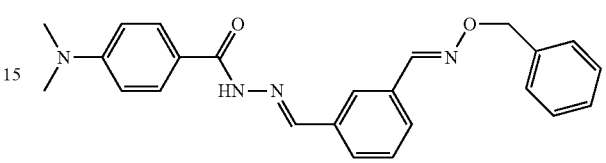

Compound 190 above was prepared according to the procedure described in Scheme VI above from 3-benzyloxyiminomethylbenzaldehyde and 4-dimethylaminobenzoic acid. ¹H NMR (DMSO, 500 MHz) 11.59 (s), 8.42 (s), 8.38 (s), 7.97 (s), 7.81 (d), 7.68 (d), 7.62 (d), 7.48 (t), 6.75 (d), and 5.20 (s).

Example 91

4-(1-Imidazolyl)benz(2E-(2-chlorophenyl)ethenylbenzylidene)hydrazide (Compound 191)

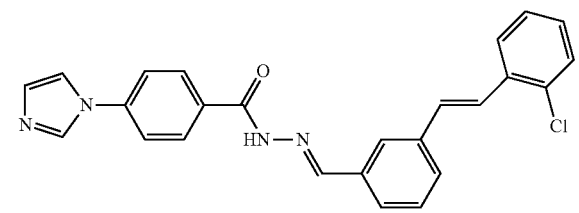 [SMILES: O=C(N/N=C/c1cccc(/C=C/c2ccccc2Cl)c1)c1ccc(-n2ccnc2)cc1]

Compound 191 above was prepared according to the procedure described in Scheme VI above from 2E-(2-chlorophenyl)ethenylbenzaldehyde and 1-imidazolylbenzoic acid. ¹H NMR (DMSO, 500 MHz) 11.97 (s), 8.52 (s), 8.41 (s), 8.07 (d), 7.97 (s), 7.92 (d), 7.72 (d), 7.68 (d), and 7.15 (s).

Example 92

4-Dimethylaminobenz(3-allyloxyiminomethylbenzylidene)hydrazide (Compound 192)

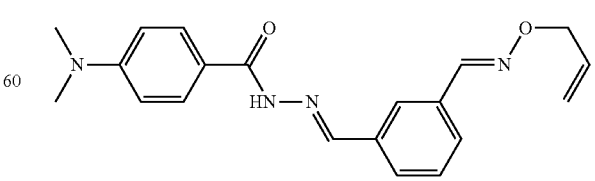

Compound 192 above was prepared according to the procedure described in Scheme VI above from 3-allyloxyiminomethylbenzaldehyde and 4-dimethylaminobenzoic acid. The molecular weight of $C_{20}H_{22}N_4O_2$ is 350.41; m/z 351.18 (MH$^+$).

Example 93

4-(1-Imidazolyl)benz(3-methoxybenzylidene)hydrazide (Compound 193)

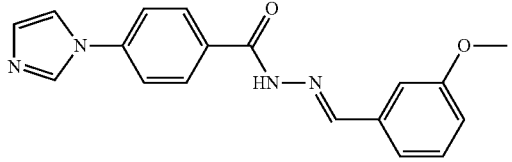 [SMILES: COc1cccc(/C=N/NC(=O)c2ccc(-n3ccnc3)cc2)c1]

Compound 193 above was prepared according to the procedure described in Scheme VI above from 3-methoxybenzaldehyde and 1-imidazolylbenzoic acid. $^1$H NMR (DMSO, 500 MHz) 11.91 (s), 8.42 (d), 8.07 (d), 7.38 (t), 7.13 (s), 7.01 (d), and 3.80 (s).

Example 94

4-(1-Imidazolyl)benz(3-benzyloxyiminomethylbenzylidene)hydrazide (Compound 194)

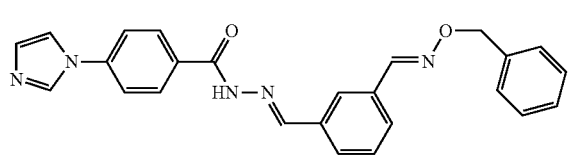 [SMILES: O=C(N/N=C/c1cccc(/C=N/OCc2ccccc2)c1)c1ccc(-n2ccnc2)cc1]

Compound 194 above was prepared according to the procedure described in Scheme VI above from 3-benzyloxyiminomethylbenzaldehyde and 4-(1-imidazolyl)benzoic acid. The molecular weight of $C_{25}H_{21}N_5O_2$ is 423.47; m/z (MH$^+$): calculated 424.17 and observed 424

Example 95

4-Dimethylaminobenz(3-(2-hydroxyethoxy)benzylidene)hydrazide (Compound 195)

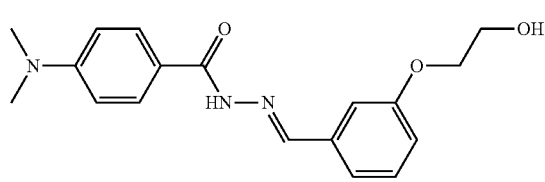 [SMILES: CN(C)c1ccc(C(=O)N/N=C/c2cccc(OCCO)c2)cc1]

Compound 195 above was prepared according to the procedure described in Scheme VI above from 3-(2-hydroxyethoxy)benzaldehyde and 4-dimethylaminobenzoic acid. $^1$H NMR (DMSO, 500 MHz) 11.58 (s), 8.39 (s), 7.80 (d), 7.34 (t), 6.98 (d), 6.74 (d), 4.90 (t), 4.02 (t), 3.75-3.69 (m), and 2.99 (s).

Example 96

2E-(4-Phenylphenyl)acryl(2-hydroxy-3-methoxybenzylidene)hydrazide (Compound 196)

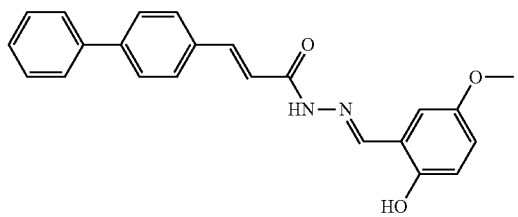 [SMILES: COc1ccc(O)c(/C=N/NC(=O)/C=C/c2ccc(-c3ccccc3)cc2)c1]

Compound 196 above was prepared according to the procedure described in Scheme VI above from 2-hydroxy-3-methoxybenzaldehyde and 2E-(4-phenylphenyl)acrylic acid. The molecular weight of $C_{23}H_{20}N_2O_3$ is 372.42; m/z (MH$^+$): calculated 373.15 and observed 373.00.

Example 97

2E-(4-Phenylphenyl)acryl(3-(2-hydroxyethoxy)benzylidene)hydrazide (Compound 197)

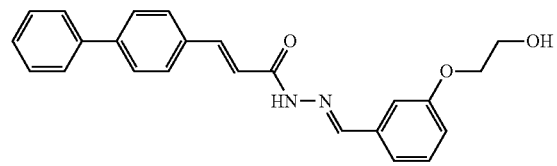 [SMILES: O=C(/C=C/c1ccc(-c2ccccc2)cc1)N/N=C/c1cccc(OCCO)c1]

Compound 197 above was prepared according to the procedure described in Scheme VI above from 3-(2-hydroxyethoxy)benzaldehyde and 2E-(4-phenylphenyl)acrylic acid. The molecular weight of $C_{24}H_{22}N_2O_3$ is m/z (MH$^+$): calculated 387.17 and observed 387.00.

Example 98

2E-(4-Phenylphenyl)acryl(4-(2-hydroxyethoxy)benzylidene)hydrazide (Compound 198)

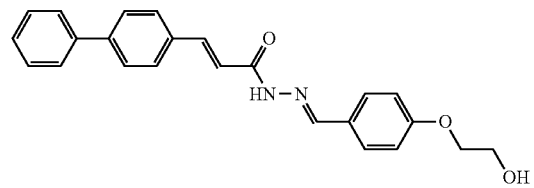 [SMILES: O=C(/C=C/c1ccc(-c2ccccc2)cc1)N/N=C/c1ccc(OCCO)cc1]

Compound 198 above was prepared according to the procedure described in Scheme VI above from 4-(2-hydroxyethoxy)benzaldehyde and 2E-(4-phenylphenyl)acrylic acid. The molecular weight of $C_{24}H_{22}N_2O_3$ is m/z (MH$^+$): calculated 387.17 and observed 386.88.

Example 99

4-(2-Hydroxyethylamino)benz(3-methoxybenzylidene)hydrazide (Compound 199)

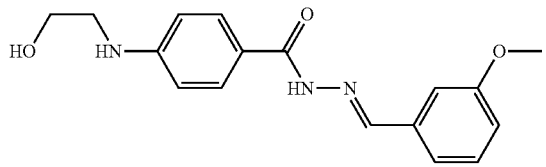 [SMILES: COc1cccc(/C=N/NC(=O)c2ccc(NCCO)cc2)c1]

Compound 199 above was prepared according to the procedure described in Scheme VI above from 3-methoxybenzaldehyde and 4-(2-hydroxyethylamino)benzoic acid. $^1$H NMR (500 MHz, CD$_3$OD) 8.25 (s, 1H); 7.77 (d, 2H, J=8.8 Hz); 7.56 (s, 1H) 7.33-7.26 (m, 2H); 6.98-6.95 (m, 1H); 6.70-6.68 (m, 2H); 3.85 (s, 3H); 3.73 (t, 2H, J=5.9 Hz); 3.30 (t, 2H, J=5.9 Hz).

Example 100

Cell Proliferation Assay

The primary testing for the exemplified compounds was performed in UT7/EPO Cell line. UT7/EPO is human leukemia cell line, obtained from Dr. Norio Komatsu (*Blood*, Vol 82 (2), pp 456-464, 1993). These cells express endogenous EPO receptor and are dependant upon EPO for growth and proliferation. Briefly, the cells were starved of EPO overnight and plated in 96 or 384 well plates. The compounds were added to the cells at 10 uM concentration. The plates were then incubated at 37° C. for 72 hours. The proliferative effect of the compounds was measured by a commercially available kit from Lonza (ViaLight Plus). The activities of the compounds are listed in the following table.

| Compound | Activity (%) | Compound | Activity (%) | Compound | Activity (%) |
|---|---|---|---|---|---|
| 108 | 2.4 | 121 | 12 | 123 | 5.1 |
| 124 | 3.4 | 125 | 15 | 126 | 3.4 |
| 127 | 6.8 | 128 | 5.6 | 129 | 23 |
| 130 | 20 | 131 | 15 | 132 | 8.7 |
| 133 | 14 | 134 | 14 | 135 | 12 |
| 136 | 4.8 | 137 | 12 | 138 | 18 |
| 139 | 7.8 | 140 | 14 | 141 | 17 |
| 142 | 6.0 | 143 | 14 | 144 | 15 |
| 146 | 4.2 | 148 | 7.1 | 149 | 9.7 |
| 150 | 4.5 | 151 | 6.3 | 152 | 6.9 |
| 153 | 5.3 | 154 | 6.7 | 155 | 11 |
| 156 | 7.9 | 157 | 9.9 | 158 | 16 |
| 159 | 8.9 | 160 | 6.1 | 161 | 12 |
| 163 | 23 | 164 | 11 | 165 | 14 |
| 167 | 11 | 168 | 11 | 170 | 4.7 |
| 171 | 16 | 172 | 9.8 | 173 | 12 |
| 174 | 19 | 175 | 4.3 | 176 | 19 |
| 177 | 9.1 | 179 | 4.3 | 180 | 3.2 |
| 181 | 4.2 | 182 | 11 | 184 | 21 |
| 185 | 16 | 186 | 9.6 | 187 | 17 |
| 188 | 5.5 | 189 | 9.1 | 190 | 20 |
| 191 | 6.2 | 192 | 5.3 | 193 | 7.3 |
| 194 | 5.2 | 195 | 7.3 | 196 | 15 |
| 198 | 4.6 | 199 | 3.0 | | |

Notes:
1) Activity represents efficacy of a compound tested at 10 uM concentration relative to EPO (100%) in the UT7/EPO proliferation assay.

What is claimed is:

1. A compound with the following structure:

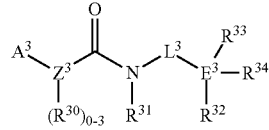

(IV)

wherein:

$R^{30}$ is selected from the group consisting of hydrogen, halogen, OR$^C$, NR$^C$R$^D$; SR$^C$, NO$_2$, CN, an optionally substituted C$_1$-C$_6$ alkyl, an optionally substituted C$_1$-C$_6$ haloalkyl, and an optionally substituted C$_1$-C$_6$ heteroalkyl;

$R^{31}$ selected from the group consisting of hydrogen, an optionally substituted C$_1$-C$_6$ alkyl, an optionally substituted C$_1$-C$_6$ haloalkyl, and an optionally substituted C$_1$-C$_6$ heteroalkyl;

$R^{32}$ is selected from the group consisting of hydrogen, halogen, NR$^C$R$^D$; SR$^C$, NO$_2$, CN, an optionally substituted C$_1$-C$_6$ alkyl, an optionally substituted C$_1$-C$_6$ haloalkyl, and an optionally substituted C$_1$-C$_{10}$ heteroalkyl;

$R^{33}$ is selected from the group consisting of hydrogen, halogen, NR$^A$R$^B$, and SR$^A$; or R$^{31}$ and R$^{33}$ are linked to form an optionally substituted heterocycle;

$R^{34}$ is selected from the group consisting of hydrogen, halogen, an optionally substituted C$_1$-C$_8$ alkyl, an optionally substituted C$_1$-C$_8$ haloalkyl, an optionally substituted C$_1$-C$_8$ heteroalkyl, (CH$_2$)$_m$R$^E$, and CH$_2$—O—(CH$_2$)$_m$R$^E$;

$R^A$ is selected from the group consisting of hydrogen, C$_1$-C$_6$ alkyl, C$_1$-C$_6$ haloalkyl, C$_1$-C$_6$ heteroalkyl, and C$_1$-C$_6$ heterohaloalkyl;

$R^B$ is selected from the group consisting of hydrogen, SO$_2$R$^F$, COR$^F$, CONR$^C$R$^D$, C$_1$-C$_6$ alkyl, C$_1$-C$_6$ haloalkyl, C$_1$-C$_6$ heteroalkyl, and C$_1$-C$_6$ heterohaloalkyl;

$R^C$ and $R^D$ are each independently selected from the group consisting of hydrogen, an optionally substituted C$_1$-C$_6$ alkyl, an optionally substituted C$_1$-C$_6$ haloalkyl, an optionally substituted C$_1$-C$_6$ heteroalkyl, and (CH$_2$)$_m$R$^E$; or one of R$^C$ and R$^D$ is an optionally substituted C$_2$-C$_6$ alkyl and the other of R$^C$ and R$^D$ is null; or R$^C$ and R$^D$ are linked to form an optionally substituted C$_3$-C$_8$ ring;

$R^E$ is selected from an optionally substituted aryl and an optionally substituted heteroaryl;

$R^F$ is selected from the group consisting of hydrogen, C$_1$-C$_3$ alkyl, C$_1$-C$_3$ haloalkyl, and an optionally substituted aryl or heteroaryl;

$A^3$ is selected from the group consisting of an optionally substituted C$_1$-C$_6$ alkyl, an optionally substituted C$_1$-C$_6$ haloalkyl, an optionally substituted C$_1$-C$_6$ heteroalkyl, a nonaromatic heterocycle, OR$^C$, NR$^A$R$^B$, and (CH$_2$)$_m$, R$^E$;

$E^3$ is a monocyclic or bicyclic aromatic ring optionally containing one or more heteroatoms, and optionally fused with a nonaromatic heterocycle or carbocycle;

$L^3$ is selected from the group consisting of null and N=CR$^C$;

$Z^3$ is selected from the group consisting of a C$_1$-C$_{12}$ alkyl, C$_6$-C$_{10}$ arylalkyl, a C$_6$-C$_{10}$ arylheteroalkyl, a C$_3$-C$_{10}$ heteroarylalkyl, a $C_3$-$C_{10}$ heteroarylheteroalkyl, and a monocyclic or bicyclic aromatic ring optionally containing one or more heteroatoms and optionally fused with a nonaromatic heterocycle or carbocycle; and m is 0, 1, or 2.

2. The compound of claim 1, wherein $R^{30}$ is hydrogen.

3. The compound of claim 1, wherein $R^{31}$ is hydrogen.

4. The compound of claim 1, wherein $R^{32}$ is selected from the group consisting of hydrogen, halogen, or $C_1$-$C_6$ alkyl, $NR^C R^D$ where $R^C$ and $R^D$ are each independently hydrogen or $C_1$-$C_6$ alkyl, $C_1$-$C_6$ alkyl, and $C_1$-$C_{10}$ heteroalkyl.

5. The compound of claim 1, wherein $R^{33}$ is selected from the group consisting of hydrogen and or $C_1$-$C_6$ alkyl.

6. The compound of claim 1, wherein $R^{34}$ is selected from the group consisting of hydrogen, $(CH_2)_m R^E$ where $R^E$ is optionally substituted phenyl, and $CH_2O(CH_2)_m R^E$ where $R^E$ is optionally substituted phenyl.

7. The compound of claim 1, wherein $A^3$ is selected from the group consisting of $C_1$-$C_6$ alkyl, a nonaromatic heterocycle, $OR^C$ where $R^C$ is hydrogen, $C_1$-$C_6$ alkyl, or $(CH_2)_m R^E$, $NR^A R^B$ where $R^A$ and $R^B$ are each independently hydrogen or $C_1$-$C_6$ alkyl, and $(CH_2)_m R^E$.

8. The compound of claim 1, wherein $E^3$ is selected from the group consisting of phenyl, naphthyl, and indolyl.

9. The compound of claim 1, wherein $L^3$ is $N=CR^C$.

10. The compound of claim 1, wherein $Z^3$ is selected from the group consisting of aryl and heteroaryl.

11. The compound of claim 10, wherein $Z^3$ is selected from the group consisting of phenyl, indolyl, and pyrazolyl.

12. The compound of claim 1, wherein:

$R^{30}$ is selected from the group consisting of hydrogen, halogen, $OR^C$, $NR^C R^D$, $SR^C$, $NO_2$, CN, an optionally substituted $C_1$-$C_6$ alkyl, and an optionally substituted $C_1$-$C_6$ haloalkyl; and $A^3$ is selected from the group consisting of an optionally substituted $C_1$-$C_6$ alkyl, an optionally substituted $C_1$-$C_6$ haloalkyl, a nonaromatic heterocycle, $OR^C$, $NR^A R^B$, and $(CH_2)_m R^E$.

13. A pharmaceutical composition comprising a physiologically acceptable carrier, diluent, or excipient; and a compound of claim 1.

* * * * *